(12) United States Patent
Fagnani et al.

(10) Patent No.: US 7,638,464 B2
(45) Date of Patent: *Dec. 29, 2009

(54) THREE DIMENSIONAL FORMAT BIOCHIPS

(75) Inventors: Roberto Fagnani, La Jolla, CA (US); Soonkap Hahn, San Clemente, CA (US); Xiaofan Dong, San Diego, CA (US); Tony Pircher, San Diego, CA (US); Sandra Matsumoto, San Diego, CA (US); Pavel Tsinberg, San Diego, CA (US)

(73) Assignee: Biocept, Inc., San Diego, CA (US)

( * ) Notice: Subject to any disclaimer, the term of this patent is extended or adjusted under 35 U.S.C. 154(b) by 473 days.

This patent is subject to a terminal disclaimer.

(21) Appl. No.: 10/054,728

(22) Filed: Oct. 25, 2001

(65) Prior Publication Data

US 2005/0037343 A1   Feb. 17, 2005

Related U.S. Application Data

(63) Continuation-in-part of application No. PCT/US00/11282, filed on Apr. 26, 2000, which is a continuation-in-part of application No. 09/299,831, filed on Apr. 26, 1999, now Pat. No. 6,174,683.

(60) Provisional application No. 60/243,699, filed on Oct. 26, 2000.

(51) Int. Cl.
    *C40B 40/00* (2006.01)

(52) U.S. Cl. ............................................ 506/13; 435/6

(58) Field of Classification Search .............. 435/4, 435/7.1, 174, 180, 181; 436/518, 528; 260/2.5 AD, 260/2.5 AY, 77.5 AM, 77.5 AP; 552/114, 552/116; 527/200, 300
See application file for complete search history.

(56) References Cited

U.S. PATENT DOCUMENTS

| | | | |
|---|---|---|---|
| 4,071,409 A | | 1/1978 | Messing et al. |
| 4,098,645 A | * | 7/1978 | Hartdegen et al. .......... 435/182 |
| 4,644,033 A | | 2/1987 | Gnanou et al. |
| 4,794,090 A | | 12/1988 | Parham |
| 5,169,720 A | * | 12/1992 | Braatz et al. ............. 428/423.1 |
| 5,175,229 A | | 12/1992 | Braatz et al. |
| 5,624,711 A | * | 4/1997 | Sundberg et al. ........... 427/261 |
| 6,087,102 A | | 7/2000 | Chenchik et al. |
| 6,174,683 B1 | * | 1/2001 | Hahn et al. .................... 435/6 |
| 6,242,246 B1 | | 6/2001 | Gold et al. |
| 6,406,921 B1 | * | 6/2002 | Wagner et al. .............. 436/518 |

FOREIGN PATENT DOCUMENTS

| | | |
|---|---|---|
| EP | 0 420 053 A1 | 4/1991 |
| EP | 1 025 860 A | 8/2000 |
| WO | WO 96/33971 A1 | 10/1996 |
| WO | WO 00/26725 A1 | 5/2000 |
| WO | WO 00/31148 A2 | 6/2000 |
| WO | WO 01/01143 A2 | 1/2001 |

* cited by examiner

*Primary Examiner*—Jeffrey S. Lundgren
(74) *Attorney, Agent, or Firm*—Fitch, Even, Tabin & Flannery

(57) ABSTRACT

A biochip is formed with a plurality of optically clear hydrogel cells attached to the top surface of a solid substrate in the form of an array. Each of the cells is formed of a hydrogel of polyethylene glycol, polypropylene glycol or a copolymer thereof having reactive isocyanate groups. Binding entities are immobilized in these cells, which entities are effective to selectively hybridize to or sequester a target biomolecule. Different binding entities are immobilized in different cells in an array to create a biochip that can be used to assay for a number of target biomolecules.

19 Claims, 5 Drawing Sheets

λ repressor
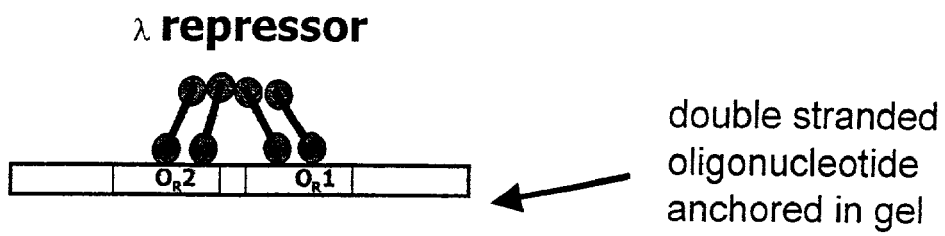
← double stranded oligonucleotide anchored in gel
FIG. 4A
wt    tctaacaccgtgcgtgttgactattttacctctggcggtgataatgg
mutant    tcttacaccgtgcgtgttgactattttacctctggcggtgaaaatgg
FIG. 4B
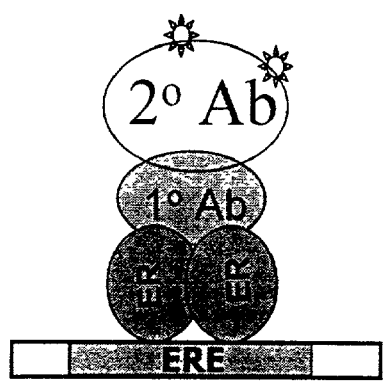
ER: estrogen receptor
ERE: estrogen response element
FIG. 5

THREE DIMENSIONAL FORMAT BIOCHIPS

This application claims priority from U.S. Provisional Application Ser. No. 60/243,699 filed Oct. 26, 2000. This application is a continuation-in-part of International Application PCT/US00/11282 filed Apr. 26, 2000, which was a continuation-in-part of U.S. Ser. No. 09/299,831, filed Apr. 26, 1999, and now U.S. Pat. No. 6,174,683. The disclosures of these applications are incorporated herein by reference.

FIELD OF THE INVENTION

Agents that selectively bind to DNA, RNA or analogs, such as peptide nucleic acids (PNAs) are of significant interest to molecular biology and medicinal chemistry as they may be developed into gene-targeted drugs for diagnostic and therapeutic applications and may be used as tools for sequence-specific modification of DNA. Additionally, such reagents may be used as tools for determining gene sequences and for functional gene analyses.

Until recently, the processes of gene discovery, characterization and functional gene analysis have been difficult and costly and have required tremendous amounts of time. However, within about the last ten years, methods of isolating arrays of biomolecules on various supports, referred to as biochips, have been developed and have been employed in DNA synthesis, sequencing, mutation studies, gene expression analysis and gene discovery. Generally the biochips are micromatrices (i.e., microarrays) of biomolecules bound to a substrate, either directly or through a linking group or, more recently, by way of a gel layer. Most biochips are designed to facilitate synthesis of biomolecules at known locations on a substrate. For example, one such biochip employs light and a series of photo-lithographic masks to activate specific sites on a substrate, such as glass, in order to selectively bind nucleic acids thereto and, subsequently, to attach additional nucleic acids to form known oligonucleotides at the desired locations. This process of using light and photolithographic masks to activate specific sites on a substrate is similar to the processes used in production of the microelectronic semi-conductor chip.

Microarrays consisting of immobilized nucleic acids, such as DNA, have demonstrated tremendous utility in the high throughput analysis and characterization of biological samples. Through analysis of such samples using the multiple combinations of biological probes on nucleic acid biochips, information is derived regarding the sample's nucleic acid components. Such biochips may be formed using simple flat plates, e.g. glass slides, or using plates having depressions or wells formed therein. Typically, various sequences of nucleic acid oligomers, DNA, i.e. single strand DNA, RNA or PNA, are immobilized in a form in which they will then hybridize to complementary sequences from the sample., see U.S. Pat. No. 6,242,246. Due to the specificity of such hybridization and the ability to rapidly examine many combinations of nucleic acid sequences, the derived data is useful in the determination of gene expression and sequence characteristics from a sample. Such data can be a key element in the determination of the genetic base of disease mechanisms and the identification of potential diagnostic and therapeutic targets.

Nucleic acid microarray methodology is able to take advantage of available DNA synthesizers, PCR methods, and developing genetic target information. However, there is also interest in extending the use of such microarrays to immobilize other binding entities of biological interest, e.g. antibodies or other proteins which might then be used to allow other high throughput analysis using nonhybridization based interactions, which could potentially provide a route to new biological insights not readily be deducible from the use of nucleic acid microarrays. Unfortunately, one would expect to encounter difficulty in fabricating a biochip that could appropriately anchor binding entities, such as proteins and peptides, because immobilization chemistries normally used to anchor such materials frequently lead to denaturation of these materials due to adherence or direct contact with a solid support surface, and it is well known that the conformation of many other binding entities, such as proteins, is key to preserving their biological activity and can be easily disrupted by immobilization through multiple moieties on the molecule. Furthermore, attachment chemistries may also be restrictive as a result of multiple, competitively active moieties that are present on many binding entities such as proteins. Moreover, often only very limited quantities of proteins isolated from tissue samples are available, and the inability to reproduce larger quantities will deter such analysis.

BACKGROUND OF THE INVENTION

First generation nucleic acid biochips are very expensive to produce, requiring large capital investments, process engineering and equipment. Furthermore, the method of forming oligonucleotides in a single layer on a substrate results in a low sensitivity biochip often requiring an expensive laser confocal fluorescence microscope for adequate detection of DNA specifically hybridized to the chip. U.S. Pat. No. 5,744,305 is an example of such a biochip.

In view of the low sensitivity of these first generation biochips, second generation biochips have been developed, such as those described in U.S. Pat. Nos. 5,736,257 and 5,847,019.

The biochips of the '257 and '019 patents employ a polyacrylamide network on top of a molecular layer of vinyl groups, thereby giving a third dimension to the gel cells. Still, as will be readily appreciated by those of skill in the art, production of biochips in accordance with the disclosures of the '257 and '019 patents is not only expensive but also time-consuming.

U.S. Pat. No. 5,552,270, issued to Khrapko, et al., describes a method of sequencing DNA which utilizes a second generation biochip comprising a solid support and a matrix that includes an array of oligonucleotides of desired lengths is attached to the support by means of a gel layer having a thickness of 30 μm or less.

Another polyacrylamide-based biochip described U.S. Pat. No. 5,770,721 is based upon the polymerization of acrylamide monomers by a free radical initiation or ultraviolet radiation process; however, this polyacrylamide-based gel biochip is constructed in a multi-step process that is lengthy and labor-intensive. Production of such a biochip requires cumbersome multi-step processing including polymerization and binding to the surface of the glass substrate; mechanical or laser cutting to form micro-squares of gel matrix on the substrate; activation step using hydrazines; and finally reaction with the oligonucleotides. Due to the polymerization process of inherent polyacrylamide gels, these steps must be performed independently. Thus, the total time required to produce a single biochip by such methods is at least about 24 to 48 hours. Furthermore, after each step, thorough washings and/or other special cares must be taken before the next step is begun. For example, the oligonucleotide derivatization step requires a long incubation period, such as twenty-four to forty-eight hours. Moreover, the potential reaction of the oligonucleotides with the hydrazine groups would form unstable morpholine derivatives, resulting in a very short shelf half-life for the biochip of approximately thirty-six hours at room temperature. Thus, there is a significant need for a simple, cost effective, rapid method for constructing a reliable multi-functional nucleic acid biochip having high sensitivity and a reasonably long shelf-life that may be used in gene discovery, gene characterization, functional gene analysis and related studies.

From the standpoint of studying protein-ligand, protein-protein, protein-DNA interaction, there are presently a number of known methods, all of which possess significant limitations in that they are either cumbersome, expensive, require large amounts of proteins or are not suitable for the rapid high throughput analysis of protein interactions.

An early method used to study protein interactions is the protein-affinity column. With this method, the capture protein is covalently immobilized to agarose beads and used to affinity-purify a target protein from a heterogeneous mixture containing many contaminating proteins through the use of affinity chromatography. This method requires relatively large amounts of capture proteins for suitable immobilization to agarose beads, and it is not suitable for the rapid high throughput screening of protein interactions.

A further method used to study protein interactions is the yeast 2-hybrid system. With this method, a target protein library is constructed in yeast. This system is designed to express these proteins of interest, with each being linked to a transcription activating region. DNA encoding for a bait protein (or a protein being examined for possible other interacting proteins) is fused to a DNA binding domain and is also expressed in the same library. A reporter gene carrying the corresponding DNA sequence is also included which codes for a detection system, such as a fluorescent protein or a protein with easily detectable biological activities. Upon binding of the target protein of interest to the bait protein, the consequent interaction of the two achieves activation of the reporter gene and results in signal generation. Even though this method may relatively frequently be used, it is slow and cumbersome, requires significant molecular biology expertise, and does not lend itself to the rapid, high throughput screening of protein-protein interaction in an economical way.

Another early method commonly employed to study protein interactions is immunoprecipitation of both the capture and the target protein, followed by analysis of the resulting complex using polyacrylamide gel electrophoresis. With this method, the capture protein is first incubated with a heterogeneous mixture of proteins allowing it to bind to its target. The resulting complex is then immunoprecipitated using antibodies raised against one protein of the pair, and the complex is separated for analysis by gel electrophoresis and followed by a detection step, e.g. staining by dye. This method is slow and cumbersome, requires significant biochemistry expertise, and likewise does not lend itself to the rapid high throughput analysis of protein interactions.

Another method used to study protein interactions is phage display. With this method, a library of proteins is expressed on the flagella of certain filamentous phage proteins expressed on the surface of a host bacterium, e.g. *E. coli* so as to provide an affinity support for such "displayed" proteins. The phage library is then exposed to a number of potential target proteins. The binding of the displayed protein to the target protein allows target identification. This method has a number of limitations, e.g. large molecular weight proteins are difficult to display, and only very few of a phage's filamentous proteins are appropriate for such use. In addition, conformational constrictions of the displayed protein have been known to decrease its affinity and consequently affect its ability to bind to its natural ligand.

The fabrication of a high-throughput-capable microarray or biochip suitable for binding such entities, e.g. proteins, will generally require the use of a method to attach proteins to the surface in a manner so that they may thereafter be used for detection by readily interacting with other materials or molecules of interest, e.g. proteins, commonly referred to as targets. For example, proteins may be bound directly to a surface treated with divalent or trivalent metal ions, such as $Cu^{2+}$ or $Fe^{3+}$, to which proteins will naturally bind with varying degrees of affinity. If targets then bind to the probes, they can be detected and identified by SELDI™ (surface-enhanced laser desorption/ionization) in combination with a mass spectrometer, as described in U.S. Pat. No. 5,719,060. In an alternative method described by G. MacBeath and S. Schreiber. (*Science* 289:1760, 2000), chemical binding is also used to attach proteins to a substrate surface, while target ligands are labeled with fluorescence tags; thus, any interaction between probes and labeled targets can be detected using a fluorescence-based slide scanner.

Because the above methods of protein immobilization to provide binding entities generally employ direct chemical conjugation of proteins onto the surface of a substrate, these methods embody a major limitation in resultant loss of protein function, due either to inappropriate chemical conjugation at active sites or to loss of original conformation. When such occurs, only a low amount of immobilized protein remains active and results in detection difficulties and low assay sensitivity. In addition, the complexity and lack of precision of these methods generally render them unsuitable for use in fabrication of high-density microarrays for high throughput use.

U.S. Pat. No. 6,087,102 describes a method which utilizes a polyacrylamide gel to create individual cells, composed of the electrophoresed protein spots, which can be subsequently crosslinked in situ into the gel to form a biochip. Limitations of the method include difficulties in preparing precise, small cells on the biochip and in potential destructive effects on the capture protein during crosslinking. U.S. Pat. No. 5,847,019 describes another approach which utilizes photopolymerizable polymers to form a patterned network layer to fabricate a biochip, using light-reactive free-radical chemistry. This photoactivation approach used for the immobilization of proteins to a biochip appears limited to certain photoactivation chemistries involving acrylamide polymers, and moreover, the use of free radical photochemistry may cause potential free radical damage to the capture proteins being used in biochips fabricated in such fashion.

The use of isocyanate-capped liquid polyurethane prepolymers to directly react with proteins to immobilize proteins within polyurethane foams is described in U.S. Pat. Nos. 4,098,645 and 3,672,955 which teach the use of isocyanate-functional hydrogel systems to bind proteins directly through their amino and hydroxyl sites to thereby form enzyme reactors and antibody/antigen based affinity columns. While the described methodology may be suitable for such purposes, these processes do not form optically clear hydrogels of controlled geometry which would be suitable for biochip use. Additionally, using such methods without inhibiting potential conjugation to protein side chains may very likely cause undesirable crosslinking of the protein to the polymer, and extensive crosslinking may diminish or destroy the native conformation of the protein and thus reduce the bioactivity of the protein which would render such process unsuitable for high precision binding assays for which biochips are used.

Despite these technical hurdles, the importance of understanding protein-protein and other comparable biomolecular interactions has made the achievement of a practical, flexible format biochip, suitable for incorporation of a number of different nonhybridization binding entities, a desired tool for a variety of research and commercial applications in biological science. In short, there exists a need for an efficient anchoring or support system which will support such entities in a manner such that they retain maximal binding activity, so as to allow for the construction of microarrays that would parallel nucleic acid arrays.

Thus, it is desirable to provide improved methods making nucleic acid biochips, as well as methods for enabling binding entities, such as proteins, to be immobilized or encapsulated in a manner which allows them to retain their native conformation and function so that they would be free to sequester targets.

SUMMARY OF THE INVENTION

The present invention provides improved biochips and rapid, simple, cost effective methods for constructing such biochips and improved assays resulting from the use of such biochips. Biomolecular probes and other binding agents can be bound prior to or simultaneously with polymerization of a particular gel, thereby permitting a simple, one or two step process to produce such a biochips which have increased sensitivity, superior stability both in use and in shelf-life, and improved cost effectiveness in manufacture.

It has now been found that by providing an appropriate gel with desired immobilization chemistries, a microarray or biochip can be created that incorporates a multitude of different, nonhybridization binding entities, as well as nucleic acid probes, in an array in a three-dimensional format suitable for high-throughput analysis of biomolecular interactions and characteristics.

The present invention provides a biochip in the form of an array of optically clear PEG or PPG-based polymeric microdroplets arranged on a solid substrate, and it provides the capability of forming as many as 1,000 individual reaction cells per square centimeter. Each cell would typically contain at least one binding entity immobilized generally within the volume of the microdroplet or upon its surface. By altering the different binding entities in the cells in the array in a known fashion, an efficient screening of biological samples or compounds for hybridization, or for binding interactions or activities, can be performed and quantitated. These cells are preferably three-dimensional in form which maximizes the amount of binding entity contained in each and thereby maximizes detection sensitivity.

The polymeric microdroplet that forms each biochip cell provides an environment particularly conducive to retaining the native conformation of an immobilized protein or peptide, for example. The resultant polymer is preferably a hydrogel that is physically and chemically stable so as to allow sequential washing and other liquid treatment steps and handlings that would be employed in the fabrication and use of a biochip. Polyethylene glycol-based prepolymers which have isocyanate-functional reactive groups are preferably utilized, and when polymerized, a polyethylene glycol hydrogel network is formed, extended and crosslinked by urethane linkages. After initiating the polymerization reaction, the prepolymer is microspotted onto a biochip substrate and allowed to fully polymerize, forming an array of three-dimensional reaction cells. The particular polymer chemistry for the cell is described in U.S. Pat. No. 6,174,683, and further technical developments have shown that polyethylene glycol, polypropylene glycol, or a copolymer fabricated three-dimensional biochips are suitable for containing a variety of nonhybridization binding entities, including proteins and peptides. Preferably, the hydrogel has sufficient active isocyanate groups thereon to both participate in the immobilization of the binding agents to the hydrogel prepolymer as well as participate in polymerization of the hydrogel and its linking to the substrate.

In one specific aspect, the invention provides a biochip comprising (a) a solid substrate having a surface; (b) at least one optically clear hydrogel cell attached to the surface of the substrate, which hydrogel cell is formed from an isocyanate-functional polymer; and (c) a binding entity immobilized within or upon said hydrogel cell, which entity is effective to selectively hybridize or to sequester a target molecule.

In another specific aspect, the invention provides a method of using a biochip to carry out a biochemical assay, which method comprises the steps of (a) providing an optically clear hydrogel biochip having a substrate with a surface to which at least two hydrogel cells are bound, each cell having a thickness of at least about 20 μm and being predominantly comprised of polyethylene glycol, polyethylene glycol or a copolymer thereof, each said hydrogel cell including a different binding entity immobilized therewithin or thereupon, (b) contacting the hydrogel biochip with an analyte solution, containing a target biomolecule under binding conditions; (c) washing the hydrogel biochip under conditions that remove non-selectively bound and unbound target biomolecule; and (d) detecting the target biomolecule bound to one of said cells.

In yet another specific aspect, the invention provides a method of preparing an optically clear isocyanate-functional hydrogel biochip having a binding entity immobilized therewithin or thereon, which entity is effective to selectively sequester or hybridize to a target biomolecule, the method comprising the steps of (a) providing an organic solvent solution of an isocyanate-functional hydrogel prepolymer; (b) providing a solution of said binding entity; (c) covalently binding said entity to the isocyanate-functional hydrogel prepolymer via reaction with not more than 15% of said reactive isocyanates; (d) initiating polymerization of the isocyanate-functional hydrogel prepolymers under conditions that will produce an optically clear hydrogel; and (e) dispensing the polymerizing isocyanate-functional hydrogel prepolymer in droplet form onto a solid substrate, such that an optically clear hydrogel polymer containing said binding entity is attached to said substrate.

In still another specific aspect, the invention provides a method of preparing an isocyanate-functional hydrogel biochip having proteins immobilized therein or thereupon which are chosen to function as capture agents, the method comprising the steps of (a) providing an organic solvent solution of an isocyanate-functional hydrogel prepolymer; (b) providing solutions of desired protein capture agents; (c) covalently binding intermediate coupling agents for said proteins to the isocyanate-functional hydrogel prepolymer; (d) initiating polymerization of said isocyanate-functional hydrogel prepolymer; (e) dispensing droplets of the polymerizing isocyanate-functional hydrogel prepolymer onto a solid substrate, such that said polymer becomes attached to said substrate; and (f) exposing individual hydrogel droplets to one of said desired protein solutions to immobilize said protein capture agents therein or thereupon via connection to said coupling agents, whereby said droplets polymerize to create a biochip having a plurality of cells with different protein captive agents.

In a further specific aspect, the invention provides a hydrogel biochip comprising (a) a solid substrate having a top surface; (b) a plurality of hydrogel cells comprising polyethylene glycol, polypropylene glycol, or copolymers thereof bound to the top surface of said substrate; (c) intermediate agents immobilized within or upon said hydrogel of said cells; and (d) different protein binding entities bound to said intermediate agents within at least several of said hydrogel cells by interaction therewith in a manner so that said protein binding entities assume their native conformations.

In a yet further specific aspect, the invention provides a method of preparing an isocyanate-functional hydrogel biochip having a plurality of cells which have binding agents immobilized therein or thereupon, the method comprising the steps of (a) providing an organic solvent solution of an isocyanate-functional hydrogel prepolymer; (b) initiating polymerization of the isocyanate-functional hydrogel prepolymer; (c) dispensing droplets of the polymerizing isocyanate-functional hydrogel prepolymer onto a solid substrate so that said droplets become attached to said substrate and form of a plurality of cells; and (d) physically immobilizing a different protein in or upon each of at least two of said cells, said proteins being chosen to function as binding agents that will selectively sequester a particular biomolecule.

BRIEF DESCRIPTION OF FIGURES

FIG. 4A is a schematic representation of the experiment described in Example 4.

FIG. 4B is a description of the two single stranded nucleic acid sequences used in Example 4.

FIG. 5 is a schematic representation of the experiment that is carried out in Example 5.

DETAILED DESCRIPTION OF THE PREFERRED EMBODIMENTS

Figure 1:
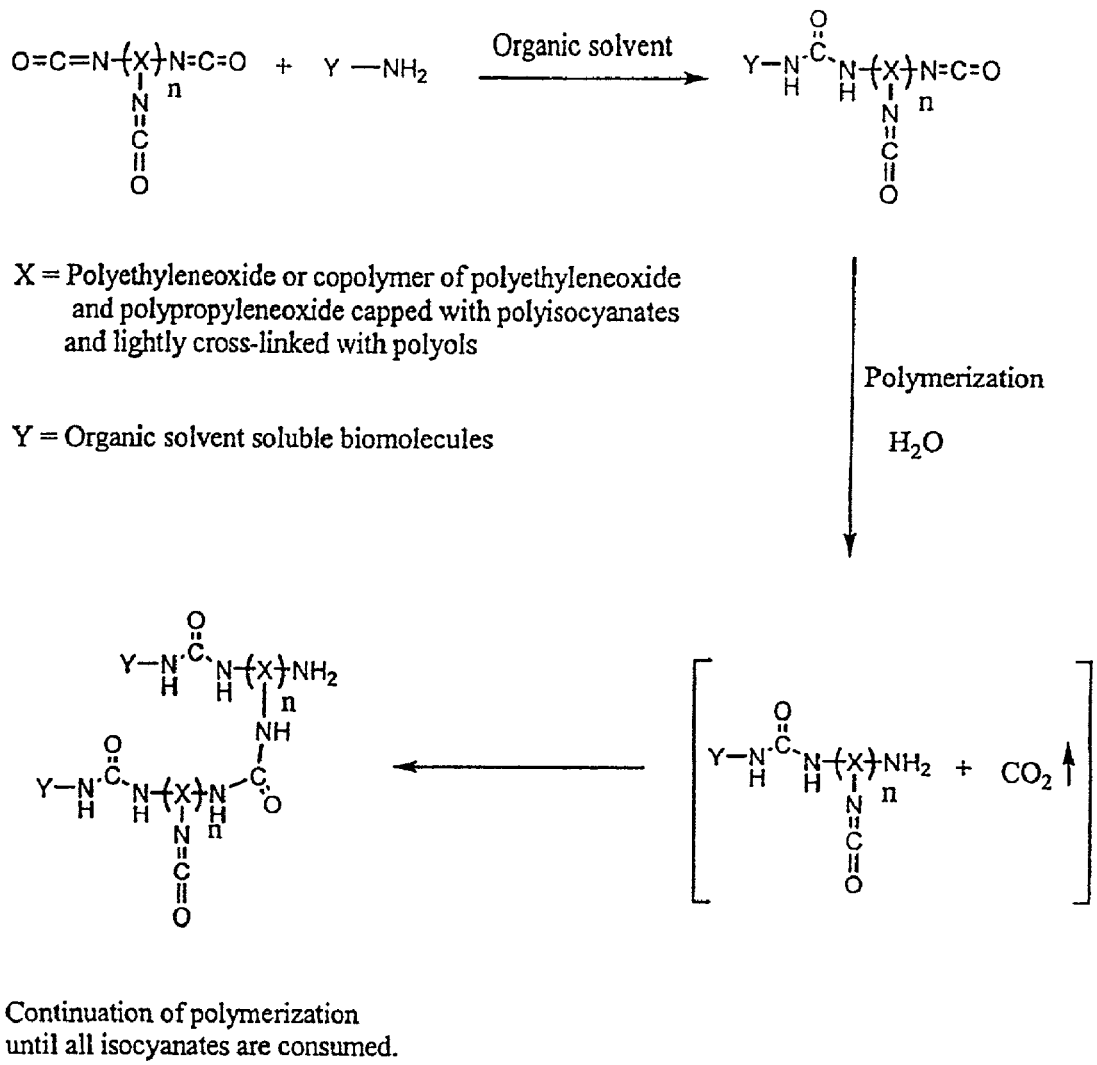
FIG. 1 is a schematic illustrating the reaction of a hydrogel prepolymer with a protein in an organic solvent followed by polymerization of the hydrogel, as a part of a process embodying various features of the present invention.

Hydrogels are a class of polymers that can provide a gel matrix that preferably has adequate pore size and high water content to permit diffusion of molecules in and out of the matrix, an ability to bind to the surface of a glass or the like, sufficient optical transparency in a fully polymerized state to minimize any optical interference with fluorescent tags, good structural integrity when fully polymerized, and adequate shelf life for normal research and clinical use. Hydrogels are hydrophilic network polymers which are glassy in the dehydrated state and swell in the presence of water to form an elastic gel. Isocyanate-functional hydrogels possess a number of characteristics that can be used to advantage for the immobilization of nucleic acid hybridization probes or other binding entities, e.g. proteins. By isocyanate-functional hydrogels are meant organic polymers that are capped with isocyanate groups that will function to carry out a desired further polymerization and also covalently bind proteins or the like, or intermediates that in turn attach proteins. For example, polyurethane polymers, which are well known in the art and which can be formed by reactions between diisocyanates and polyether or polyester polyols, can provide suitable hydrogels for this purpose.

Prepolymers are preferably used as a starting material to form biochips using these isocyanate-functional hydrogels, and preferably these prepolymers are formulated to provide hydrated polyurethane, polyurea-urethane and/or polyurea polymeric gels. Hydrogel polymers have been prepared from various prepolymers and used for a wide variety of other applications. Typically, hydrogels are formed by polymerizing a hydrophilic monomer in an aqueous solution under conditions such that a lightly cross-linked prepolymer is initially formed having a three-dimensional polymeric network which gels in concentrated form. Polyurethane hydrogels are formed by polymerization of isocyanate-end-capped prepolymers by the creation of urea and urethane linkages.

Suitable isocyanate-functional prepolymers are often prepared from relatively high molecular weight polyoxyalkylene diols or polyols which are reacted with bi-functional or multi-functional isocyanate compounds. The preferred prepolymers are made from polyoxyalkylene diols or polyols that may comprise homopolymers of ethylene oxide units or block or random copolymers containing mixtures of ethylene oxide units and propylene oxide or butylene oxide units. In the case of block or random copolymers, at least 75% of the units should preferably be ethylene oxide units. Alternatively, homopolymers of polypropylene oxide may also, but less preferably, be employed. The polyoxyalkylene diol or polyol molecular weight is preferably from 2,000 to 30,000, and more preferably from 5,000 to 30,000. Suitable prepolymers may be prepared by reacting selected polyoxyalkylene diols or polyols with polyisocyanate, e.g. at an isocyanate-to-hydroxyl ratio of about 1.2 to about 2.2 so that essentially all of the hydroxyl groups are capped with polyisocyanate. The isocyanate-functional prepolymer preferably should contain active isocyanates in an amount of about 0.1 meq/g to about 1.2 meq/g, and preferably about 0.2 meq/g to about 0.8 meq/g. In general, a fairly low molecular weight prepolymer, e.g. less than 3,000 MW, should preferably contain a relatively high isocyanate content (about 1 meq/g or higher). The polymerization rate of such a prepolymer should be controlled so as not to polymerize too rapidly to effectively microspot, and in this respect, high molecular weight prepolymers containing a relatively low isocyanate content are generally preferred.

Such high molecular weight prepolymers are often prepared by either of two general methods, but others as known in the art can also be used: (1) a polyol (triol or higher) having a molecular weight of at least 2000, is reacted with a polyisocyanate such as isophorone diisocyanate, or (2) a diol having a molecular weight of at least 2000 is reacted with a polyisocyanate and a cross-linking agent, such as glycerol, trimethylolpropane, trimethylolethane, triethanolamine or an organic triamine.

Aromatic, aliphatic or cycloaliphatic polyisocyanates may be used. High molecular weight aliphatic isocyanate-capped prepolymers typically gel to a hydrated polymer state in about 20 to 90 minutes, whereas prepolymers capped with aromatic polyisocyanates gel much more rapidly. Examples of suitable bi- and multi-functional isocyanates are as follows: toluene-2,4-diisocyanate, toluene-2,6-diisocyanate, isophorone diisocyanate, ethylene diisocyanate, ethylidene diisocyanate, propylene-1,2-diisocyanate, cyclobexylene-1,2-diisocyanate, cyclohexylene-1,4-diisocyanate, -phenylene diisocyanate, 3,3"-diphenyl-4,4"-biphenylene diisocyanate, 1,6-hexamethylene diisocyanate, 1,4-tetramethylene diisocyanate, 1,10-decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylene diisocyanate, 4-methoxy-1,3-phenylene diisocyanate, 4-chloro-1,3-phenylene diisocyanate, 4-bromo-1,3-phenylene diisocyanate, 4-ethoxyl-1,3-phenylene diisocyanate, 2,4-dimethyl-1,3-phenylene diisocyanate, 2,4-dimethyl-1,3-phenylene diisocyanate, 5,6-dimethyl-1,3-phenylene diisocyanate, 1,4-diisocyanatodiphenylether, 4,4'-diisocyanatodi-phenylether, benzidine diisocyanate, 4,6-dimethyl-1,3-phenylene diisocyanate, 9,10-anthracene diisocyanate, 4,4'-diisocyanatodibenzyl, 3,3'-dimethyl-4,4'-diisocyanatodiphenylmethane, 1,6-dimethyl-4,4'-diisocyanatodiphenyl, 2,4-diisocyanatostibene, 3,3'-dimethoxy-4,4'-diisocyanatodiphenyl, 1,4-antracenediisocyanate, 2,5-fluoronediisocyanate, 1,8-naphthalene diisocyanate, 2,6-diisocyanatobenzluran, 2,4,6-toluene triisocyanate, p,p',p"-triphenylmethane triisocyanate, trifunctional trimer (isocyanurate) of isophorone diisocyanate, trifunctional biuret of hexamethylene diisocyanate, trifunctional trimer (isocyanurate) of hexamethylene diisocyanate, polymeric 4,4'-diphenylmethane diisocyanate, xylylene diisocyanate and m-tetramethyl xylylene diisocyanate.

Capping of the selected diols or polyols with polyisocyanates to form prepolymers may be effected using stoichiometric amounts of reactants. The isocyanate-to-hydroxyl group ratio may vary as known in this art but should preferably be about 1 to about 3, and more preferably about 1.2 to about 2.2. The capping reaction may be carried out using any suitable conditions, such as at about 20° to about 150° C., under dry nitrogen, for about 2 hours to about 14 days, and preferably in the absence of a catalyst. The preferred temperature is about 60° to 100° C., and the reaction terminates when the isocyanate concentration approximates theoretical values.

Preferred prepolymers include polyethylene glycol that is end-capped with toluene diisocyanate: a copolymer of ethylene oxide and propylene oxide (optionally with trimethylolpropane) and toluene diisocyanate; toluene diisocyanate-polyethylene glycol-trimethylopropane, methylene diisocyanate-methylene homopolymer; polymeric methylene diisocyanate-polyethylene glycol; polymer of ethylene oxide-propylene oxide-trimethylolpropane and isophorone diisocyanate, and polyethylene glycol trilactate and toluene diisocyanate. Suitable prepolymers of the above types are available from Hampshire Chemical Corp. of Lexington, Mass. as HYPOL PreMA® G-50, HYPOL® 2000, HYPOL® 3000, HYPOL® 4000 and HYPOL® 5000, which formulations generally include copolymers of polyethylene oxide and a minor amount of polypropylene oxide.

All things considered, the main chain of the hydrogel polymer is preferably comprised of polyethylene glycol, polypropylene glycol, or a copolymer of polyethylene glycol and polypropylene glycol. While not to be constrained by any theoretical mechanism, it is believed that the non-ionic, hydrophilic properties of polyethylene glycol and polypropylene glycol hydrogels provide for low levels of non-specific binding of analyte to the hydrogel and also for good compatibility with the immobilized biomolecules so as to maintain native conformation and bioreactivity thereof. Isocyanate-functional hydrogels advantageously absorb large quantities of liquid quickly and in a relatively uniform manner such that the basic overall shape of the gel material is maintained. Further, the moisture absorbed by these materials is retained in the absorbent material even under an applied pressure. Polyurethane-based isocyanate-functional hydrogels of this general type are described in U.S. Pat. Nos. 3,939,123 (Mathews, et al.), 4,110,286 (Vandegaer, et al.) and 4,098,645 (Hartdegan, et al.). Such polyurethane-based hydrogels have been extensively used as surface coatings and to form flexible or rigid foams; they have also been used to form foams for enzyme reactor systems.

In a preferred embodiment, biochips are made using an isocyanate-functional hydrogel that is based on a diol or triol of a high molecular weight polyethylene oxide, polypropylene oxide, or a copolymer of polyethylene oxide and polypropylene oxide, capped with water-active diisocyanates, and which may be optionally lightly cross-linked with a suitable cross-linker. It is preferred that the quantity of active isocyanates present in the prepolymer is predictable, for example preferably between about 0.1 and about 1 meq/g, but more preferably not greater than about 0.8 meq/g. Generally preferred diisocyanates include aromatic-based diisocyanates, such as toluene diisocyanate or methylene diphenylisocyanate, as well as aliphatic diisocyanates, such as isophorone diisocyanate. Preferably, about 15% to about 5% of the reactive isocyanates in the polymer are used to provide sites for immobilizing binding entities, and more preferably 10% or less of the reactive isocyanates in the prepolymer are employed to immobilized binding entities. The polymerization of the prepolymer for biochip creation, which may be preformulated in a water-miscible organic solvent, takes place by the formation of urea linkages which occur upon the simple addition of water.

The term binding entity is used to refer to material capable of interacting in a specific fashion with one or more target molecules to hybridize or to physically sequester a target molecule by a mechanism other than hybridization. These binding entities include nucleic acids, such as DNA, RNA and PNA which bind via hybridization; nonhybridization binding entities include, but are not limited to, biological material, such as proteins including receptors, peptides, enzymes, enzyme inhibitors, enzyme substrates, immunoglobulins, e.g. antibodies, antigens, lectins, modified proteins, modified peptides, double-stranded DNA, biogenic amines and complex carbohydrates; they may also include synthetic molecules, e.g. drugs and synthetic ligands, designed to have specific binding activity of this type. By "modified" proteins or polypeptides is meant those proteins or peptides having one or more amino acids within the molecule altered by the addition of new chemical moieties, the removal of existing chemical moieties or some combination of both removal and addition. This alteration may include both natural and synthetic modifications. Natural modifications include, but are not limited to, phosphorylation, sulfation, glycosylation, nucleotide addition, and lipidation. Synthetic modifications include, but are not limited to, chemical linkers to facilitate binding to the hydrogel, and the addition of fluorescent dyes, microstructures, nanostructures, e.g. quantum dots, or other synthetic materials. In addition, modification may include the removal of existing functional moieties, e.g. hydroxyl, sulfhydryl or phenyl groups, or the removal or alteration of native side chains or the polypeptide amide backbone. Examples of complex carbohydrates include, but are not limited to, natural and synthetic linear and branched oligosaccharides, modified polysaccharides, e.g. glycolipids, peptidoglycans, glycosaminoglycans or acetylated species, as well as heterologous oligosaccharides, e.g. N-acetylglucosamine or sulfated species. Also included are synthetic modifications thereof, such as the addition of molecules such as drugs, ligands, dyes or other agents useful for the purpose of screening and quantitation. Examples of naturally-occurring complex carbohydrates are chitin, hyaluronic acid, keratan sulfate, chondroitan sulfate, heparin, cellulose and carbohydrate moieties found on modified protein such as albumin and IgG. Combinations of two or more of such entities might be immobilized at some locations on the microchip array, which combinations might be added as one mixture of two entities or may be added serially.

A binding entity can be directly or indirectly immobilized in each cell or microspot either prior to, during, or after polymerization of the cell material. Indirect immobilization contemplates the employment of an intermediate agent that is first linked to the hydrogel and possibly a second intermediate agent that is, in turn, linked to it. For example, a first or primary intermediate agent that is encapsulated into the hydrogel matrix might be an antibody directed against calmodulin. Once calmodulin is bound to the antibody, the calmodulin serves as a second intermediate agent as it is utilized, in turn, to sequester calmodulin-binding-proteins, such as the calcium/calmodulin dependent kinase II. This approach to attaching CaM kinase II (as it is commonly referred to) to the hydrogel provides a gentle way of anchoring the protein via a naturally-occurring binding motif, i.e. through the calmodulin protein. The CaM kinase II is now free to probe analyte solutions, for example for the purpose of examining regulatory events on the CaM kinase II (phosphorylation, dephosphorylation) or for searching for possible docking proteins or other intracellular trafficking proteins. Alternative ways of anchoring the CaM kinase II may lead to its loss of function or to other deleterious effects.

In describing the interaction between an immobilized entity and the target as sequestering or nonhybridization binding, it is meant that two or more molecules adhere or bind together in a specific and selective fashion, typically by covalent or non-covalent bonds (e.g., by van-der-Waals forces and/or ionic interactions). The specific target can be a simple molecule that may be present in a complex mixture of biological or synthetic materials. The sequestering or binding may be of an extended nature, e.g. covalent modification or antibody-antigen interaction, or it may be transient, e.g. as would occur during a phosphorylation event. Nonhybridization DNA binding entities include, but are not limited to, synthetic and natural double-stranded polymers of deoxyribonucleotides, synthetic and natural poly ribonucleotides, aptamers, and synthetic polynucleotides having one or more modified or non-naturally occurring chemical entity. This alternative use of DNA as a binding/sequestering agent is in contrast to conventional nucleotide hybridization arrays which typically employ single strands of DNA (oligonucleotides or cDNA) to which target DNA hybridizes. Double-stranded DNA might be employed to interact with (as opposed to hybridizing) a suitable biomolecule, such as a DNA binding protein, a transcription factor, e.g. estrogen receptor, or a synthetic drug or molecule, so as to bind or sequester that biomolecule. As an example, general transcription factors, such as TBP or SP 1, or gene specific transcription factors, such as nuclear hormone receptors, can be attracted to and sequestered by helical, double stranded DNA. Aptamers are described in U.S. Pat. No. 5,840,867 where they are indicated to function much like monoclonal antibodies.

Alternatively, an embodiment may employ an initial binding entity which is physically co-polymerized within the gel matrix, e.g. select antibodies or other selective binding agents, e.g. aptamers, wherein one or more different antibodies would be immobilized in each cell of an array. Upon subsequent application of a complex mixture of biological materials to such an array, the unique binding attributes of these immobilized antibodies within each cell will "self-sort" such a complex mixture and create a new array which "self-assembles"; the new array will be complementary to the initial binding entities. For example, an antibody against a specific antigen is immobilized within each gel microspot during polymerization; thereafter, specific protein or peptide antigens are provided to bind to each of the cognate antibodies by exposing a mixture of protein or peptide antigens to such an array. One example of the use of such an intermediate antibody array is to self-sort a complex mixture of proteins from cell extracts without requiring individual isolation of each protein. Such an array thus formed might then be employed to assess what the effect would be on each site of exposure to an added protein kinase or other protein-modifying moiety. This concept might be extended to examine whether such modifying activities would be influenced by drugs or other added chemical compounds.

As a further alternative, other binding entities may be located or anchored within a cell of a biochip array after polymerization through the use of intermediate agents that will be initially immobilized. For example, a suitable intermediate, such as Protein A, is immobilized during polymerization; thereafter, a desired immunoglobin capture agent is bound to the immobilized Protein A by controlled exposure to the immunoglobin in solution.

In still other embodiments, the initial immobilized binding entities may be subsequently modified. Such modifications may include (a) biological modifications, e.g. phosphorylation, glycosylation, acetylation, methylation, ubiquitination, lipid modification and ADP-ribosylation, or (b) non-biological modifications, e.g. fluorescent dye modification, biotinylation, alkylation and abnormal residue incorporation, as well as by conjugation with another protein or enzyme to yield an altered final form of the array. As yet another embodiment, double-stranded nucleic acid oligonucleotides (or polymers) are immobilized during polymerization; thereafter, the desired proteins are bound to such nucleic acids by nucleic acid sequence-specific protein interaction, to produce a self-assembled protein-nucleic acid complex array.

Figure 2:
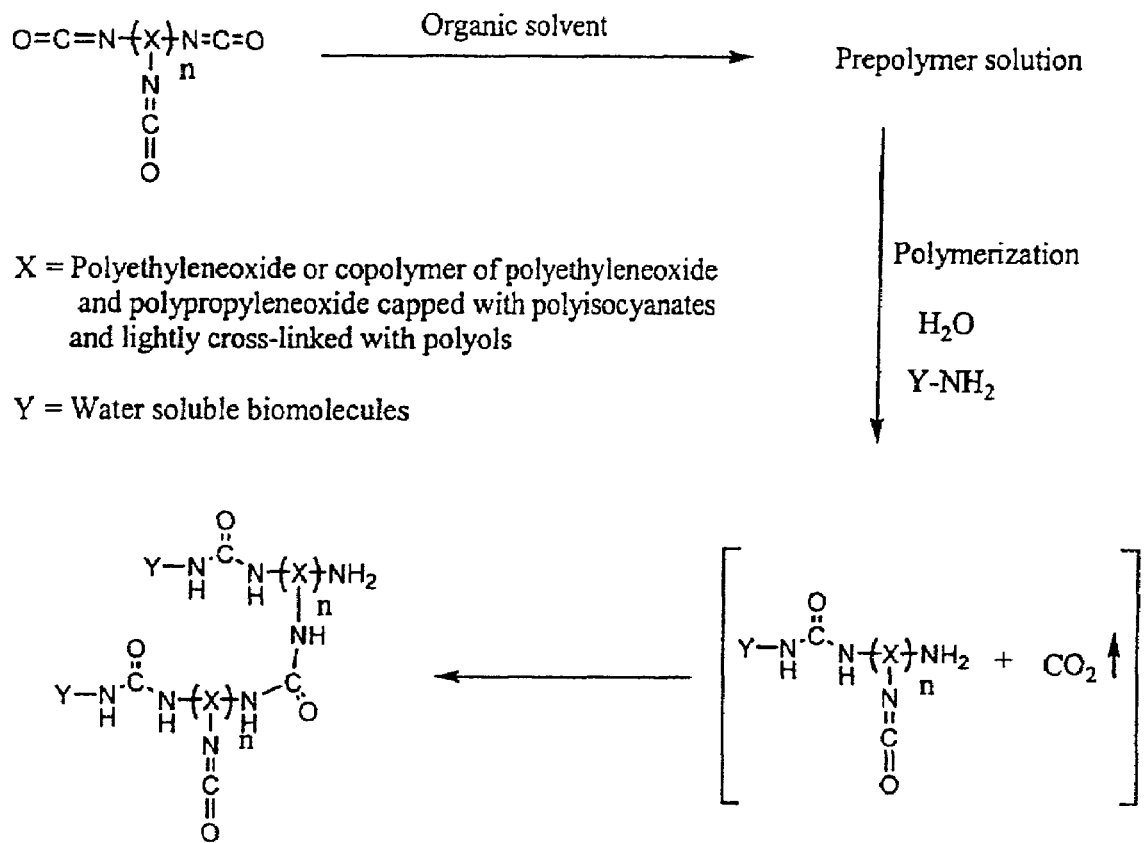
FIG. 2 is a schematic illustrating an alternative reaction of a hydrogel prepolymer with a protein in water during polymerization of the hydrogel.

By first reacting the prepolymer with the binding entity in an aprotic solvent, the binding entity is effectively immobilized onto the prepolymer, and this procedure may have a number of advantages in the preparation of the hydrogel. It may help to subsequently generate a homogeneous solution of the prepolymer in water, and it may also serve to slow down the generation of carbon dioxide during the polymerization step as lowering the viscosity of the polymerizing mixture allows $CO_2$ to slowly effervesce. In the polymerization of the polyurethane-based hydrogels, for example, some gaseous carbon dioxide is generated by the reaction of water with the isocyanate groups of the hydrogel prepolymer. Such reaction is illustrated in FIGS. 1 and 2, and it may be advantageous to control the generation of carbon dioxide gas and its escape from the gel when a biochip is prepared from such a prepolymer. If polymerization occurs too quickly in a highly viscous mixture, carbon dioxide gas which is generated is unable to escape and can become trapped within the gel. Such can result in a discrete foam matrix, which may be a problem for continuum of the gel matrix, and it may interfere with the optical transparency. In biochip design, the greater of the optical transparency, the more accurate will be the detection of fluorescence which would be indicative of successful binding to a target. One way of controlling the generation of carbon dioxide is by maintaining the pH at about 8.5 or below to control the reaction rate and thus the diffusion of carbon dioxide in the polymerizing solution.

A further advantage of derivatizing the hydrogel in an aprotic solvent is an enhancement of the optical clarity or transparency of the hydrogel by minimizing any precipitation of the prepolymer. Another way to achieve slow polymerization of the gel and, therefore, slow generation of $CO_2$, to assure continuous and transparent gel matrix is to maintain the ratio of aprotic solvent to water at at least about 0.25 to 1 and preferably higher, e.g. 0.3-0.35 to 1. Derivatization and polymerization of the hydrogel is generally accomplished in about thirty minutes of such ratios. The quantity of binding entity bound to the prepolymer of any cells is easily adjusted by simply varying the amount of binding entity added to the reaction (for example, from about 10 fmol up to about 1 pmol of protein for each microdroplet), thereby permitting close control over the amount of binding entities immobilized within each hydrogel microdroplet.

Ease of diffusion of a prospective target molecule or other secondary binding entity through the gel to interact with an intermediate or primary binding entity immobilized within the gel matrix will be determined, in some part, by the percentage of hydrogel prepolymer in the solution that is employed. Originally, the employment of 5% solution of prepolymer for formulating hydrogel droplets was found to be adequate to create cells wherein nucleic acid probes were immobilized; however, at 5% level, diffusion of larger molecules, such as proteins, into the polymerized hydrogel is slower than desired. It has now been found that a lower percentage of prepolymer, e.g. 3.5% is preferred to facilitate passage of larger biomolecules into the hydrogel. However, below about a 3% prepolymer solution, the resultant gel may lack sufficient structural integrity and/or adequate polymerization to be useful. Thus, for many applications, such as those employing antibodies as a visualization tool, the preferred range of polymer is felt to be between 3% and 5%. Other applications and uses, such as those for examining molecules smaller in size than a typical antibody, e.g. IgG (or larger, e.g. when the gel encloses or anchors microspheres), may respectively employ a higher or lower percentage of polymer in the solution.

When the hydrogel is first derivatized with protein and then deposited onto the solid substrate, after initiation and before completion of polymerization thereof, delivery may be accomplished by any convenient method; for example, a conventional microspotting machine which deposits gel to form an array of microdroplets may be used. While such a gel may inherently non-covalently attach to some substrates, a substrate surface is generally derivatized prior to addition of the hydrogel to achieve firm attachment of the gel to the substrate. For example, in one preferred embodiment where glass is used as the substrate, the glass is derivatized with amine prior to deposit of the polymerizing hydrogel. The polymerizing hydrogel, derivatized with protein, then binds strongly to the substrate when it is deposited onto the derivatized glass substrate, via reaction of some of its active isocyanate groups with amines now located on the surface of the glass. This provides covalent attachment of the hydrogel to the substrate, and preferably about 5% or less of the active isocyanate groups originally in the prepolymer are used for this function.

In certain embodiments, partial initial blocking of the binding entity may be preferred to maximize efficient immobilization of the binding entity. The reactivity of the isocyanate prepolymer with certain chemical moieties that a particular binding entity may include, e.g. primary amines, may result in excess crosslinking between the binding entity and polymer, and such may lead to denaturation of the binding entity or may lower its binding affinity for its target compound. Such might be avoided or limited by protecting at least some of these moieties during polymerization; deprotection after polymerization would then return the functionality and utility of the binding entity within the array, i.e. de-blocking after polymerization would allow the binding entity to assume its native conformation. Such blocking/de-blocking may be accomplished by either covalent or non-covalent means. For example, when using antibodies as the binding entity, an antigen recognition site susceptible of becoming crosslinked to the polymer is incubated with an uncross-linkable peptide (or other epitope mimic) prior to mixing with the prepolymer. Such peptide or epitope mimic would protect the antigen recognition site from conjugation with the reactive isocyanate groups during the polymerization process. Following polymerization, such peptide would be released from the antibody, e.g., by brief exposure to acid, pH 3.0, thus re-exposing the antigen recognition site of the antibody. Similar mechanics can be employed to protect select sulfhydryl moieties or amines on binding entities; these could use well known reversible chemical derivatization to protect these functionalities while polymerization proceeds.

It was first noted that polyethylene glycol might be added as a thickening agent to facilitate a more linear expansion during polymerization. It has since been discovered that other compounds may be added to the hydrogel during polymerization to maintain the stability and native activity of the binding entities, e.g. proteins. Non-binding additives may be optionally included in the prepolymer mix for stabilization of the binding entities. These additives include, but are not limited to, glycerol, Ficoll, and ethylene glycol as well as saccharides such as mannitol, sucrose and trehalose. The use of other bulk agents, including non-specific (non-binding) proteins, such as bovine serum albumin, can also be employed to aid in the activity of entities, e.g., proteins, when it is desired to limit the extent of crosslinking to the hydrogel.

Another optional use of additives is to employ materials that create zones or domains within the polymerizing hydrogel. Upon completion of polymerization, these materials are either dissolved or diffused away in aqueous solution, leaving larger pores, vacuoles or channels within the hydrogel polymer than would otherwise be present in the absence of these materials. The presence of such larger pores creates a larger surface area on and within the hydrogel cell, providing an increased capacity for binding biomolecules or the like that might be too large to easily diffuse through the hydrogel matrix.

The hydrogel polymer is suitable for immobilizing a wide variety of other binding entities, including, but not limited to, materials such as synthetic molecules, drugs, non-peptide receptor ligands, mixed organic/inorganic species, e.g. metal porphyrins, and inorganic materials, e.g. zeolites. In one preferred embodiment, these entities are used to sequester compounds from solutions based upon specific interactions between the binding entity and the analyte species. In another preferred embodiment, these binding entities transiently interact with species in solution. Such is the case when the binding entity serves as a selective substrate for a reactive process, e.g. phosphorylation, methylation, cleavage or other forms of modification. In a yet another embodiment of the invention, the incorporated materials may be involved in the catalysis of reactions. Such catalytic materials may be useful in bioreactors. Alternatively, an array of different catalytic entities may be used to screen for the most efficient catalytic entity. In general, these hydrogels formulated with such binding entities are useful for a variety of tasks, including, but not limited to, bioassays, materials screening and sensors.

Figure 3A:
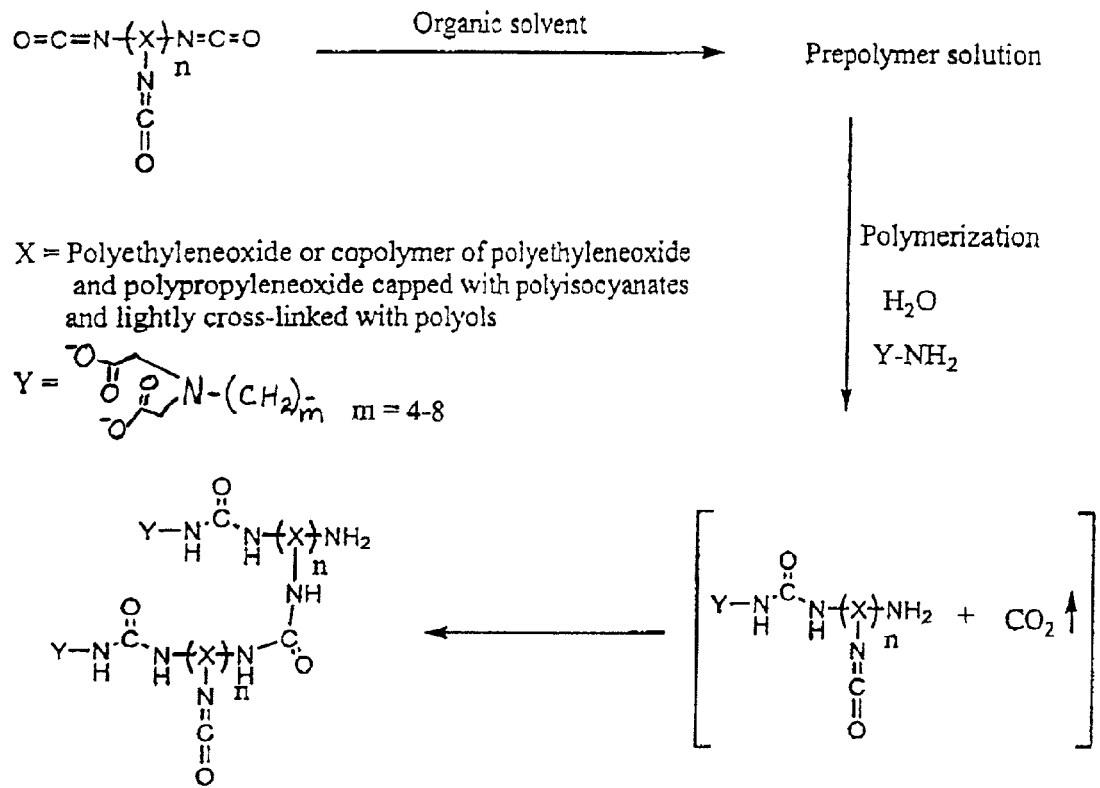
FIGS. 3A and 3B are schematic illustrations of another alternative reaction of a hydrogel prepolymer with a chelating agent, followed by chelating with a metal and subsequently binding with a protein that contains multiple histidines at its tail.
Figure 3B:
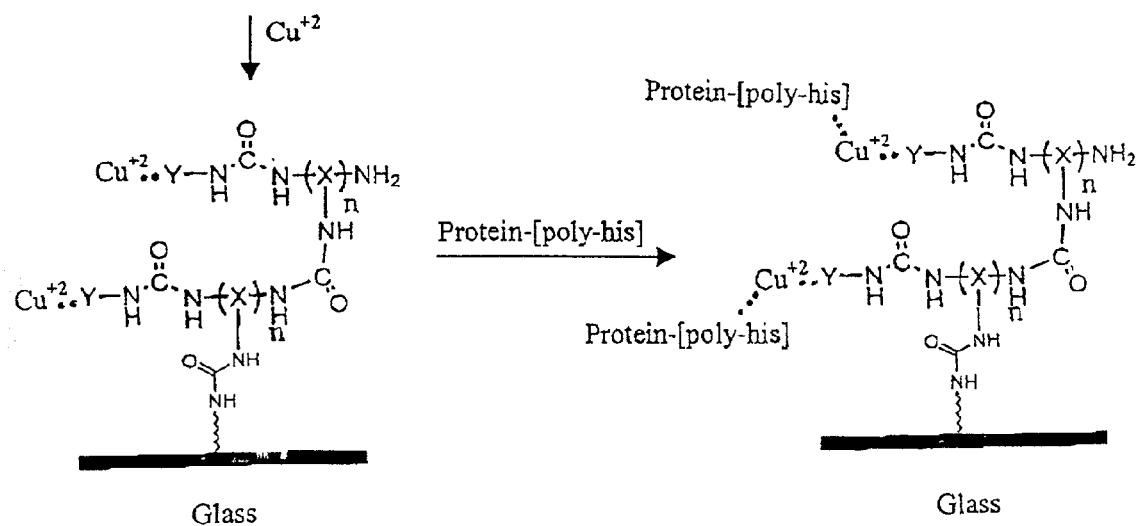

Alternatively, a non-biological compound, such as a tridentate or tetradentate metal chelating agent, e.g. iminodiacetic acid or nitrilotriacetic acid, having a proper linker of amine-derivatized $C_4$-$C_8$, is immobilized within the hydrogel as an intermediate binding agent, either prior to or during polymerization as schematically depicted in FIG. 3A. The desired binding entity, e.g. a protein, is preferably synthesized or modified so as to have a multiple histidine-containing sequence, e.g. as a terminus on the tail or head of the protein, and such can then be immobilized to each cell of the biochip by exposure along with a divalent or trivalent metal ion, such as $Cu^{2+}$ or $Fe^{3+}$, so as to allow chelation with such a terminal residue to physically immobilize the protein within the hydrogel by linking to the immobilized chelating agent, as schematically depicted in FIG. 3B. By exposing each cell to a particular binding entity, e.g. a different protein capture agent, a protein chip stable for analytical use is formed. One advantage of employing an intermediate agent in creating such a polymer microdroplet is the greater assurance that potential denaturation of a particularly susceptible protein is avoided so that the conformation and configuration of the ultimate binding entity protein remains unaltered. Also, fabrication may be simplified by the use of the same chelating agent for creating each microdroplet or cell in a particular protein microarray and then subsequently linking the binding agents thereto.

The biochip substrate may consist of a variety of materials and formats which are conducive to automated handling during a binding assay and later detection of target molecules binding to the individual cells. Although solid flat plates, e.g. glass slides, are suitable, plates that have depressions or wells formed therein to hold individual cells may be used. An optically transparent substrate, such as glass or clear polystyrene, will allow for transmission light detection through the cells and is convenient for detection modalities using fluorescence or optical absorption. Due to the high binding capacity of three-dimensional hydrogel cells, reflective optical methods are also possible and allow the use of opaque substrates. The use of rigid substrates would allow for precision of alignment during the detection phase of analysis using a biochip, but such may not be necessary if proper alignment is incorporated into the cells to facilitate detection. For example, a flexible format, such as a tape or filament, could be precisely detected in a scanning fashion similar to the use of magnetic tape. While optical methods and suitable substrates are preferred due to their simplicity, other biochemical detection methods might alternatively be used, e.g. the detection of radioactive agents. Generally, any number of cells can be provided on a biochip, e.g. from 1 to 1000. To assist automated handling, often multiples of 96 cells may be used; for example, 384 cells may be provided in an array on a 3 in (7.6 cm)×5 in (12.7 cm) plate. Although multiple cells are preferably used, a biochip utilizing only a single cell may be satisfactory in certain situations.

In certain embodiments, it may be preferable to load the binding entity into the hydrogel cell after polymerization of the hydrogel cell. Simple diffusion may be an ineffective tool by which to accomplish this. Small molecules that rapidly diffuse into the hydrogel may, in the course of subsequent use, readily diffuse out of the hydrogel, thereby causing the loss of these binding entities. Therefore, in the case of such readily diffusable agents, e.g. small molecules and peptides, it is preferable to have a mechanism to covalently conjugate such agents to the polymeric matrix after diffusion into the matrix. One preferred means to accomplish this utilizes a moiety suitable for performing crosslinking, e.g. photoactivated or chemical crosslinking reagents, contained either within the polymer as part of its composition or linked to the small molecule diffusing into the polymer.

In contrast, larger binding entities, e.g. proteins and large segments of DNA, may not efficiently migrate into the hydrogel matrix by passive diffusion. In order to facilitate the diffusion of larger species into the matrix, an electric field is applied in such a fashion as to cause the controlled migration of species having a net charge, e.g. proteins, within a solution having a pH value different from the isoelectric point of the protein. This process is termed "electrophoresis". If the hydrogel cell is within the migration path of the charged species, the charged species undergoes an additional force supplied by the applied electric field in addition to passive diffusional forces, thereby accelerating its insertion into the hydrogel cell. An advantage of this electric-field-facilitated diffusion is that these larger binding entities will not readily, passively diffuse out of the hydrogel matrix during subsequent assay steps.

Following polymerization of the hydrogel cell, the substrate surface not occupied by the hydrogel cells may be treated with agents or materials to reduce subsequent non-specific or non-desired adherence of assay reagents, target molecules or other materials. This is especially useful in those applications where assay reagents may potentially non-specifically bind to the surface, and thus might substantially reduce the effective concentration of the assay reagents or target molecules in solution. Alternatively, such treatment may be employed to decrease the amount of background signal observed from the surface and thereby increase the effectiveness of the hydrogel cell for assay purposes.

Treatments for such exposed surface regions include the application of reagents that react with primary amines which are present as an initial layer or coating on the substrate surface. These reagents include, but are not limited to, activated polyethylene glycol polymers having at least one end containing a reactive moiety, e.g. isocyanate, that will covalently bind to a primary amine; and small, non-polymeric molecules functionalized with nucleophile-reactive moieties, such as succinyl esters. The case in the silanization of glass or the use of standard blocking reagents, e.g. bovine serum albumin, customarily employed to reduce background signals as well known to those skilled in the art of molecular biology applications may alternatively be used.

Advantageously, all reactions involved in this system, namely (1) the derivatization of hydrogel prepolymer either directly with the protein probe or with an intermediate agent, (2) the polymerization of hydrogel and (3) the binding of derivatized hydrogel to the substrate surface, involve the formation of strong urea or urethane (carbamate) bonds. These bonds endow the microdroplet array with mechanical integrity and significantly increase the half-life of the biochip.

In certain preferred embodiments described hereinafter, the hydrogel microdroplets, following polymerization on the substrate, are preferably at least about 20 μm thick, more preferably at least about 30 μm thick and most preferably at least about 50 μm, e.g. 50 μm to 100 μm, thick. Furthermore, the microdroplets are generally elliptical in shape, as opposed to the square gel cells previously used in some systems. The overall larger size of the gel microdroplets (or cells) permits a significant increase in the quantity of binding entities immobilized therein, thereby reducing the lower detection limit of the biochip and facilitating its use. By decreasing the viscosity of the polymer solution and with appropriate modifications to dispensing mechanisms heretofore used for microspotting onto on to a biochip substrate, smaller individual cells can be produced enabling very high-density biochip arrays. If substrates having wells are employed, the microdroplets should be deposited upon the bottoms of the wells.

The following examples illustrate several applications relating to protein chips. A representative biochip suitable for study of protein-protein interactions is illustrated by binding calmodulin to calcinerine in a calcium-dependent manner. A biochip suitable for protein-DNA interactions is illustrated by the binding of lambda repressor protein to DNA. It should of course be appreciated that these biochips are suitable for antigen-antibody interactions and for other such interactions as mentioned hereinbefore that may not be specifically illustrated in the working examples.

EXAMPLE 1

Preparation of a DNA Biochip and Test

A solution of 0.025 g of Hypol PreMa G-50 was prepared in 0.15 g acetonitrile. Next, a solution of 1 mg DNA (0.3 µm), having hexaneamine at its 5' end and having the sequence $NH_2(CH_2)_6$-CATTGCTCAAAC-3' (SEQ ID No:1), in 0.32 g of a 50 mM $NaHCO_3$ aqueous buffer at pH 8.0 was prepared. The DNA solution was added to the prepolymer solution and thoroughly mixed. Droplets of the resulting solution were manually spotted on a silanated glass slide using a capillary microtube. As a negative control, hydrogel droplets containing no DNA were spotted next to the DNA-containing hydrogel droplets.

The glass slide, having the hydrogel droplets thereon, was submersed into washing buffer (10 mM sodium phosphate buffer with 0.5 M NaCl and 0.1% SDS at pH 7.0) for 30 minutes to remove organic solvents and block the remaining active sites to prevent non-specific binding of test DNA. Next, the slide was treated with 1 mg of a complementary fluorescence-labeled DNA, 3'-TAGTAACGAGTTTGCC-5'-Fluorescein (SEQ ID NO:2), in 600 µL hybridization buffer (10 mM sodium phosphate buffer with 0.5 M NaCl and 0.1% SDS at pH 7.0) at room temperature, for 1 hour. Non-specifically bound DNA was removed by washing for two hours in washing buffer. The slide was observed with a hand-held fluorescence detector (Model UVGL-25, UVP). The complementary, test DNA diffused into the hydrogel microdroplet and hybridized to the gel-bound DNA probe sequence resulting in a strong fluorescent signal, but it was washed away from the negative control droplet, demonstrating the reliability and usefulness of the present hydrogel biochips in DNA hybridization assays.

EXAMPLE 1A

Preparation of an Array DNA Biochip and Test in Human β-globin Gene Sequence Detection A DNA biochip was prepared as follows:
1. The following two reactant solutions were prepared:
   Solution A=0.1 g Hypol Pre-Ma G-50 in 0.33 g acetonitrile and 0.33 g NMP (Weight ratio of 4.5:15:15)
   Solution B=1 mg of oligonucleotide in 1 ml of 50 mM borate buffer at pH 8.0
2. Solution A (34.5 parts) was mixed with Solution B (65.5 parts), and the resultant solution microspotted onto a glass slide. Microspotting was performed with an open configuration pin, CT MicroPipets DP-120 µm, supplied by Conception Technologies.
3. The microspotted slides were placed into a controlled humidifier chamber for one hour and then washed with a washing buffer for 10 minutes, completing the preparation of the biochips.

Testing of such a biochip is performed by hybridization with a target sample carrying a fluorescent tag or the like at different concentrations in a hybridization buffer system for 20 minutes to 2 hours, proportional to the molecular weight of the target. Any non-specifically bound target is washed away with the hybridization buffer, and the biochip is then scanned to detect the bound target by optical fluorescence.

To validate the performance of these biochips which carry DNA probes, the following twenty 12-mer oligonucleotides, derivatized with primary amine at the respective 5' end using standard amidite chemistry, were immobilized on separate hydrogel cells as a part of a biochip made in this manner:

| G1 | 5'-CCTAAGTTCATC-3' | (SEQ ID NO:3) |
| G2 | 5'-TATCTCTTATAG-3' | (SEQ ID NO:4) |
| G3 | 5'-CTATCGTACTGA-3' | (SEQ ID NO:5) |
| G4 | 5'-TTCCTTCACGAG-3' | (SEQ ID NO:6) |
| G5 | 5'-ATTATTCCACGG-3' | (SEQ ID NO:7) |
| G6 | 5'-ATCTCCGAACTA-3' | (SEQ ID NO:8) |
| G7 | 5'-CCTTATTATGCA-3' | (SEQ ID NO:9) |
| G8 | 5'-ACGCTTCCTCAG-3' | (SEQ ID NO:10) |
| G9 | 5'-GACTTCCATCGG-3' | (SEQ ID NO:11) |
| G10 | 5'-CGTACCTTGTAA-3' | (SEQ ID NO:12) |
| G11 | 5'-CTAAACCTCCAA-3' | (SEQ ID NO:13) |
| G12 | 5'-CTAGCTATCTGG-3' | (SEQ ID NO:14) |
| G13 | 5'-TAATTCCATTGC-3' | (SEQ ID NO:15) |
| G14 | 5'-ATTCCGATCCAG-3' | (SEQ ID NO:16) |
| G15 | 5'-TTAGTTATTCGA-3' | (SEQ ID NO:17) |
| G16 | 5'-AAGTTCATCTCC-3' | (SEQ ID NO:18) |
| G17 | 5'-TTCATCTCCGAA-3' | (SEQ ID NO:19) |
| G18 | 5'-CCGAACTAAACC-3' | (SEQ ID NO:20) |
| G19 | 5'-AACTAAACCTCC-3' | (SEQ ID NO:21) |
| G20 | 5'-CTAAACGTCCAA-3' | (SEQ ID NO:22) |
| G21 | Blank hydrogel | |

A target 30-mer DNA sample from the sequence of the human β-globin gene was synthesized and labeled with a tagging molecule, i.e. fluorescein, at its 5' end using standard amidite chemistry. The sequence of this target sample is the following: 5'-(Fluorescein)-TTGGAGGTTTAGTTCG-GAGATGAACTTAGG-3'(SEQ ID NO:23).

The sequences of G1, G6, G11, G16, G17, G18 and G19 are fully complementary to different regions of the target sample. The sequence of G20 has an internal one-base pair mismatch from that of G11. The results of the testing are set forth in Table A which follows:

TABLE A

The Intensity of Fluorescence Depending on Sequences

| | Oligonucleotide | | | | | | | |
|---|---|---|---|---|---|---|---|---|
| | G1 | G6 | G11 | G16 | G17 | G18 | G19 | G20 |
| Intensity | 1528 | 2713 | 5630 | 650 | 841 | 2098 | 6066 | 2181 |
| Standard deviation | 77 | 151 | 238 | 164 | 127 | 354 | 638 | 225 |

As seen in Table A, the hybridization discrimination of perfect match (G11) and one-base pair mismatch (G20) was excellent (Fluorescence intensity of 5630 vs 2181). The non-related oligonucleotides of G2, G3, G4, G5, G7, G8, G9, G10, G12, G13, G14 and G15, as well as the blank hydrogel cell, demonstrated intensity just above background showing minimum non-specific binding to the hydrogel.

EXAMPLE 2

Use of Additives (glycerol/trehalose) to Enhance Bioactivity

The following example shows that unreactive proteins, simple carbohydrates and humectants have a protective effect on hydrogel-immobilized antibody activities of these biochips, enhancing overall signal and assay performance.

Panel A —Trehalose. In this experiment, aliquotes of a trehalose stock solution, 50% w/v D(+) trehalose dihydrate in 50 mM sodium borate buffer, pH 8.0, were added to 50 μl final volume hydrogel formulation. The formulation also included 3.5 weight % final concentration HYPOL PreMA® G-50 hydrogel prepolymer (premixed stock solution containing HYPOL, acetonitrile, N-methyl-2-pyrrolidinone at a w/w/w ratio of 1:3:3, respectively), anti-transferrin (4 mg/ml phosphate buffered saline IX (PBS), 2 μl bovine IgG (50/mg/ml in PBS and 1.25% glycerol). The amount of trehalose was varied from 0 to 10 μl, corresponding to a final w/v percentage of 0, 1%, 2%, 5% and 10% trehalose. A blank hydrogel spot which did not contain protein was also included. These test solutions were spotted as three pins per sample with two spots per pin onto an amine-coated glass slide. Test protein encapsulated was anti-transferrin, and the system was incubated with Cy3 fluorescent dye-labeled transferrin (Amersham, approximately 0.1 μg/ml in PBS containing 0.1% Triton X100 (PBST), and 1% bovine serum albumin (BSA)) at 45° with shaking for the indicated times. Following incubation, the slide was washed 2×10 minutes in PBST and then imaged using a ScanArray Lite slide scanner. The blank hydrogel spots had no detectable signal, and 0% trehalose had a weak signal. 1% and 2% trehalose were a little more intense, 5% had higher signal yet, and 10% had the strongest signal. These results indicate that the addition of trehalose had a positive effect on the bioactivity of the test antibody in the hydrogel.

Panel B —Glycerol. Glycerol, dissolved as a 20% stock in pH 8.0 sodium borate buffer, was added to the above-mentioned hydrogel formulation containing 3.5% final HYPOL PreMA® G-50, anti-transferrin, bovine IgG, and 5% trehalose, to a final concentration of 0%, 0.5% and 1%, e.g. 0, 1.25 μl and 2.5 μl of stock glycerol. As in the above-mentioned assay, the Cy3 fluorescent dye-labeled transferrin system was used for assay. For Panel B, for each half percent increase in glycerol, there was an increase in signal intensity, evidencing a positive effect upon the antibody activity.

Using the methodology described above, mouse IgG was immobilized in 3%, 4% and 5% hydrogel, respectively. BSA was included in as a separate spot as a non-specific binding control. Following curing of the polymer, the array was incubated with a solution of rhodamine-labeled rabbit anti-mouse antibody for one hour, then washed. The rabbit anti-mouse antibody bound to mouse IgG antibodies, and the extent of binding was determined by fluorescence at each location using a ScanArray Lite slide scanner. Under identical binding conditions and binding time, the lower percentage hydrogel spots displayed stronger binding signals; this is indicative of a faster diffusion rate of the rhodamine-rabbit-anti-mouse IgG into the hydrogel matrix at these lower percentages.

EXAMPLE 3

Use of Coating to Block Non-Specific Binding/Lower Background of Slide

N-hydroxysuccinimidyl active ester (NHS) activated polyethylene glycol (PEG) polymer, mPEG-SPA-NHS 5K (Shearwater Corporation) was dissolved in 0.05 M sodium bicarbonate, pH 8.25, buffer to a final PEG concentration of 50 mg/ml. Corning aminosilane slides were used for surface grafting of the polymer. Grace-Biolabs hybridization chambers (SA500-3LCLR) were used as reaction chambers. To coat the surface, three slides were treated with the PEG solution for 3 hours on a shaker at room temperature (NSH rt), three slides were treated for three hours at 45° C. (NSH 45), and an additional slide was treated for 3 hours at 45° C. in DI water as a control.

After PEG treatment, the hybridization chambers were removed, and the slides were washed in PBS for 10 minutes, followed by distilled water wash for 10 minutes, followed by air-drying. Cy3-labeled glial-derived neurotrophic factor was dissolved in PBST. Slides were incubated at room temperature for 1 hour. They were then washed in PBS for 10 min, and distilled water for 10 min. The slides were then scanned using a ScanArray Lite slide scanner. A 5-10 fold lower background intensity signal following treatment under both sets of conditions indicates the effectiveness of the PEG coating in reducing non-specific absorption of fluorescent materials onto the surface.

EXAMPLE 4

Protein-DNA Interaction on a Biochip

In the following experiment, single-stranded DNA is first linked to the hydrogel followed by hybridization to create double-stranded binding entities which then are effective to sequester target proteins as schematically shown in FIG. 4A. 5' amino-modified, single-stranded bacterial λ repressor binding sequence $O_R 2 O_R 1$ (wt) and its mutant (mut) carrying a single base mutation at the binding site (sequences are shown in FIG. 4B where the binding sites are underlined) are printed on amino-silanated slides at 130 μM in 3.75% HYPOL™. The printed spots are enclosed in individual hybridization chambers and are allowed to hybridize to their corresponding complementary sequences at 1 μM in 3×SSC, 0.1% Triton X-100, 5 mM $MgCl_2$ at 45° C. for 18 hours. The resultant double-stranded DNA are then incubated with 1.5 μg/ml Cy3-labeled bacterial phage lambda repressor λCI in binding buffer (50 mM Tris.HCl (pH 7.6), 100 mM NaCl, 1 mM $CaCl_2$, 0.1 mM EDTA, 0.1 mg/ml BSA, 2.5 μg/ml poly (dA-dT), 0.05% Tween 20, 1 mM DTT) at room temperature for 2 hours. The Cy3-labeled λCI is removed at the end of the binding reaction, and the slide is rinsed briefly with binding buffer then deionized $H_2O$ ($dH_2O$) and imaged by a GSI laser scanner. In a separate slide, the double-stranded DNA is stained with SYBR Gold (Molecular Probe) according to manufacturer's protocol and visualized by a GSI laser scanner for its total DNA content.

Binding of the Cy3 labeled λ repressor to its native operon dsDNA sequence was shown by the gain of fluorescent signal in the corresponding spots. The absence of a strong fluorescence in the mutant spots indicated that the interaction is sequence-specific. Comparison of the SYBR Gold (a double-stranded DNA stain) stained fluorescence of the printed slides, with the Cy3 fluorescence from λ repressor, confirms that it is the sequence-specific λ repressor-λ operon interaction rather than any non-specific protein linking to unevenly printed DNA that gives rise to the Cy3 signal associated with the wild type $O_R2O_R1$ sequence. A hundred-fold difference in signal intensity between linking to the wild type sequence as compared to the mutant sequence confirms the specificity of the reaction to the double-stranded DNA that was immobilized within the hydrogel matrix.

EXAMPLE 5

Protein-DNA Interaction on a Biochip

In this experiment, double-stranded DNA is pre-hybridized before polymerization and immobilization, which is followed by target protein binding.

Double-stranded (ds) DNA biochips can also be made by directly printing 5' amino-modified prehybridized dsDNA. This procedure contrasts with the previous example where a single-stranded DNA was printed, and the cognate oligonucleotide was subsequently hybridized to this printed oligonucleotide to form the binding entity.

In this example, an estrogen receptor (ER), a 53 kD protein, binds as a homodimer to its consensus estrogen response element (ERE). The wild-type ERE sequence differs from the mutant sequence by four nucleotides in a region known to be critical for binding by the receptor. The wild-type sequence is a 32-base oligomer with the sequence 5'-tttacggtagaggtcactgtgacctctacccg-3'(SEQ ID NO:24). The mutant sequence differs by four oligonucleotides (underlined) and has the sequence 5'-tttacggtagaggtcactgtatggtctacccg-3' (SEQ ID NO:25). To produce dsDNA for printing, 5 µl of a 650 µM stock of each of the amine-linked oligonucleotide of interest and its complementary oligonucleotide are diluted 1:650 (65 µM final concentration) in 40 µl DNA hybridization buffer, pH 8 (3×SSC, 5 mM $MgCl_2$) for a final reaction volume of 50 µl. The reaction product is incubated at 95° C. for 10 min and then chilled on ice for 3 min. Ten microliters of this double-stranded DNA is printed within 450 µm hydrogel spots using a solution consisting of 3.75% polymer, 0.5% glycerol and 50 mM sodium borate buffer, pH 8.0. Following 1 hour of blocking with a 1% BSA in PBST solution, 1 µl of transcription factor in the form of ER concentration 1.153 µM was diluted in appropriate binding buffer (10% glycerol, 10 mM HEPES, 30 mM KCl 0.1 mM EDTA, 0.25 mM DTT, 1 mM $Na_2HPO_4$, pH 7.9) and allowed to bind to the dsDNA for 1 hour at room temperature; a 10-min wash with PBST then followed. The ER-ERE complex was next incubated with a 1:100 dilution of a rabbit anti-ERβ antibody for 1 hour at RT, followed by a 30-min wash with PBST. This was followed by incubation with a 1:1000 dilution of goat anti-rabbit IgG-Cy3 conjugate for 1 hour at RT, followed by a 30-min PBST wash. The overall experiment is diagrammatically depicted in FIG. 5. The slide was rinsed with $dH_2O$ and air dried before imaging with a ScanArray Lite scanner. Signal analysis was performed using ArrayPro 4.0 software. An increased signal observed from spots containing the wild-type sequence as compared to the mutant sequence signal, which resembles the control, indicates the retention of linking specificity by the estrogen receptor for its target sequence in the hydrogel matrix.

EXAMPLE 6

Antigen-Biochip

This experiment shows that the hydrogel platform can be used as a matrix for anchoring still other binding entities, i.e. antigens. Antibody-antigen interactions are routinely employed in a variety of biological assays, and the ability to anchor either component (antibody or antigen) is a desirable feature in a support. In this example, an antigen is anchored within the hydrogel matrix.

Using the methodology described in Example 2, the protein antigen, human transferrin (0.2 mg/ml), was directly immobilized at different dilutions in 3.3% hydrogel with 5% trehalose, 2 mg/ml BSA onto an amine-coated glass slide. After blocking with 5% non-fat dry milk, the slide was incubated for 1 hour with mouse ascites fluid containing anti-human transferrin at the varying concentrations. After incubation, the slide was washed three times for 10 mins with PBST. The bound, mouse, anti-transferrin antibody was visualized by incubating the slide with Cy3-labeled donkey anti-mouse IgG, followed by laser scanner imaging. A linear dose response over three orders of magnitude of dilutions, i.e. 0.1 to 0.001, was observed. This dose-response relationship indicates the functionality of the antigen anchored within the hydrogel matrix and the permeability of the hydrogel matrix supporting sequential diffusion of antibodies into the matrix as part of the overall assay methodology.

EXAMPLE 7

Antibody-Biochip

As noted in the previous example, antibody-antigen reactions are routinely employed in biological assays. In this example, an antibody is anchored within the hydrogel matrix, as opposed to anchoring the antigen in Example 6.

Anti-human transferrin, anti-BSA and anti-PSA antibodies (0.4~0.8 mg/ml) were immobilized in 3.3% hydrogel in the presence of 5% trehalose, 2 mg/ml bovine IgG and 0.5% glycerol on amino-silanated glass slides, following the methodology of Example 2. The slides were then incubated at room temperature overnight with Cy3-labeled individual antigens at a concentration of 1 mg/ml in PBST containing 1% BSA. Bound proteins were visualized by laser scanner imaging after an extensive wash with PBST. The presence of labeled target proteins at the sites of the corresponding antibodies on the microarray indicated the retention of functionality of the antibodies in the hydrogel matrix.

EXAMPLE 8

Multiple Layers ELISA Assay

The ability to support more complex binding interactions may also be a desired feature for the hydrogel matrix. In this example, use is made of the hydrogel to anchor an antibody as a first binding entity. Subsequent specific localization of its antigen is followed by additional binding events for the purpose of visualization, and this shows the biocompatibility of the hydrogel with respect to multiple binding events by proteins, as well as confirming maintenance of protein functionality.

Rat anti-mouse IL-2 monoclonal capture antibody (BD, Pharmingen) was directly immobilized in 3.3% hydrogel with 5% trehalose, 2 mg/ml Bovine IgG on an amino-silanated glass slide, as per the methodology outlined in Example 2. The slide was incubated with diluted culture medium from phytohemaglutinin-stimulated mouse LBRM-33 4A1 cells or unstimulated cells, for one hour with proper mixing at room temperature. After two 15-minute wash PBST washes, the slide was incubated with biotinylated rat monoclonal anti-mouse IL-2 detection antibody (BD, Pharmingen) at room temperature for one hour. Free antibody was removed by three PBST washings of 15 minutes each. Horseradish peroxidase-conjugated streptavidin was subsequently added to the slide for another hour of incubation at room temperature. Cy3-tyramide substrate from a TSA reagent system is added to the slide to fully cover all printed spots, after an extensive wash of streptavidine-HRP following recommended protocol. After washing off unreacted substrate, the slide is analyzed by laser scanner imaging. An eight-fold increase in fluorescent signal indicates the presence of bound antigen by the anchoring antibody within the hydrogel.

EXAMPLE 9

Multiple Layers Small Molecule Mediated (CaM/calcineurin)

Figure 6:
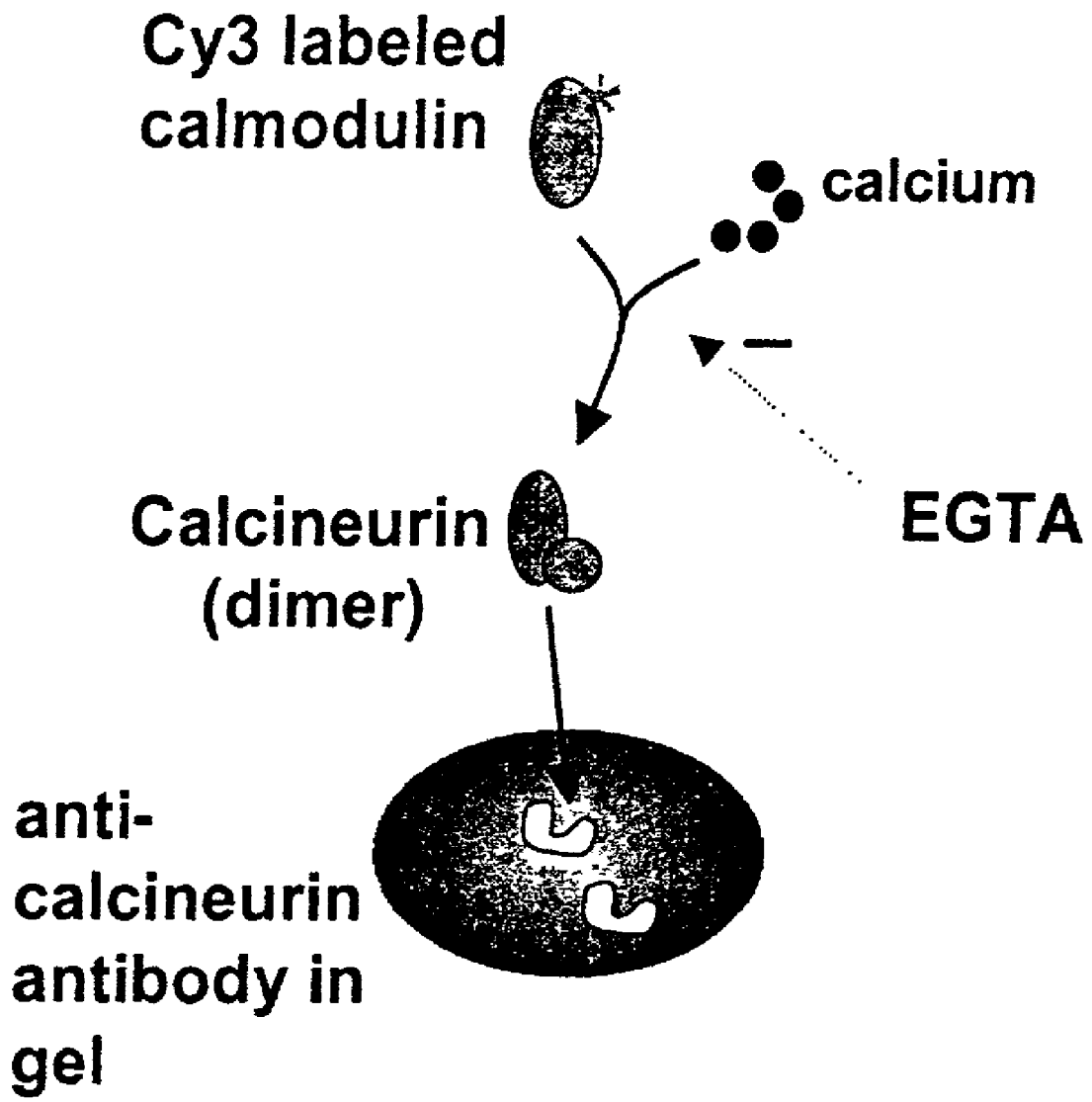
FIG. 6 is a schematic representation of the experiment that is carried out in Example 9.

Complex interactions between multiple proteins are frequently difficult to accomplish on support surfaces; however, the following example demonstrates the use of multiple protein interactions mediated by small molecules and is schematically illustrated in FIG. 6.

Mouse anti-bovine brain calineurin monoclonal antibody (0.4 mg/ml, Sigma), sheep anti-bovine calmodulin antibody (0.2 mg/ml, Chemicon) and control bovine IgG (0.4 mg/ml) were respectively and directly immobilized in 3.3% hydrogel with 5% trehalose and 2 mg/ml bovine IgG onto an amine-coated glass slide, as per the methodology of Example 2. The slide was subsequently incubated with 0.1 mg/ml bovine calcineurin in 20 mM HEPES (pH 7.6), 130 mM KCl, 0.1% Triton X-100, 10 µg/ml polyglutamic acid overnight, after 5% dry milk blocking. Cy3-labeled chicken calmodulin is allowed to bind to the calcineurin-treated slide in the presence of 1 mM $CaCl_2$ or 5 mM EGTA in PBST, 1% BSA at room temperature for one hour. The bound calmodulin was visualized by laser scanner imaging at the Cy3 excitation and emission wavelengths. A six-fold increase in signal intensity shown at the anticalcineurin antibody location in the presence of calcium as compared to in its absence (i.e. in the presence of EGTA) indicates the ability of the hydrogel matrix to support complex biomolecular interactions involving both proteins and small molecules.

EXAMPLE 10

Specific Detection of Tyrosine Phosphorylated Peptides on a Biochip

The hydrogel matrix is compatible with a wide variety of binding entities and assay formats. In this example, the use of a phosphorylated amino acid within a peptide binding entity is shown.

Each peptide was printed onto a slide as two quadruple pairs beside each other at 40 µM concentration; the peptides were immobilized in 3.5% HYPOL™ containing 0.5% glycerol, as per the methodology of Example 2. The peptides listed in Table B which follows were printed on the slides.

TABLE B

| No. | Substrate | Amino Acid Sequence | SEQ ID NO. |
|---|---|---|---|
| 1 | insulin receptor fragment | NH-thr-arg-asn-ile-pTyr-gln-thr-asn-tyr-tyr-arg-lys-OH | 26 |
| 2 | PTP Substrate II | NH-asp-ala-asp-glu-PTyr-leu-ile-pro-gln-gln-gly-OH | 27 |
| 3 | PTP Substrate I | NH-glu-asn-asp-pTyr-leu-ile-asn-ala-ser-leu-OH | 28 |
| 4 | insulin receptor fragment | NH-thr-arg-asn-ile-tyr-gln-thr-asn-tyr-tyr-arg-lys-OH | 29 |
| 5 | pp60 c-src (521-533) | NH-thr-ser-thr-gly-pro-gln-tyr-gln-pro-gly-glu-asn-leu-OH | 30 |
| 6 | pp60 c-src (521-533) (phosphorylated) | NH-thr-ser-thr-glu-pro-gln-pTyr-gln-pro-gly-gly-asn-leu-OH | 31 |
| 7 | PDGF receptor substrate | NH-ser-val-leu-pTyr-thr-ala-val-gln-pro-asn-glu-OH | 32 |
| 8 | pp60 (v-scr) autophosphorylation site | NH-arg-arg-leu-ile-glu-asp-asn-glu-pTyr-thr-ala-arg-gly-OH | 33 |
| 9 | RrreepSEEEAA-OH | NH-arg-arg-arg-glu-glu-glu-pSer-glu-glu-glu-ala-ala-OH | 34 |
| 10 | Angiotensin II substrate | NH-asp-arg-val-pTyr-Ile-his-pro-phe-OH | 35 |
| 11 | pp60C-src | NH-thr-ser-thr-glu-pro-gln-tyr-gln-pro-gly-glu-asn-leu-OH | 36 |
| 12 | RR-SRC | NH-arg-arg-leu-ile-glu-asp-ala-glu-tyr-ala-ala-arg-gly-OH | 37 |
| 13 | SRC Kinase Substrate | NH-arg-arg-leu-ile-glu-asp-ala-glu-pTyr-ala-ala-arg-gly-OH | 38 |
| 14 | PDGF receptor substrate | NH-asn-pTyr-ile-ser-lys-gly-ser-thr-phe-leu-OH | 40 |
| 15 | Anti-estrogen phospho peptide | NH-cys-asn-val-val-pro-leu-pTyr-asp-leu-leu-leu-glu-OH | 41 |

TABLE B-continued

| No. | Substrate | Amino Acid Sequence | SEQ ID NO. |
|---|---|---|---|
| 16 | Tyrosine kinase substrate | NH-arg-arg-leu-ile-glu-asp-asn-glu-thr-thr-ala-arg-gly-OH | 42 |
| 17 | Tyrosine kinase substrate | NH-arg-arg-leu-ile-glu-asp-ala-glu-thr-ala-ala-arg-gly-OH | 43 |
| 18 | Retroviral protease substrate | NH-thr-phe-gln-ala-tyr-pro-leu-arg-glu-ala-OH | 42 |
| 19 | Angiotensin II antipeptide | NH-gly-gly-val-tyr-val-his-pro-val-OH | 44 |
| 20 | Angiotensin I | NH-asp-arg-val-tyr-ile-his-pro-phe-his-leu-OH | 45 |

The trivial abbreviations are used with pTyr=phosphotyrosine and pSer=phosphoserine.

In all following incubation steps, the glass slides were incubated on a rocker in glass slide-staining dishes. The peptide biochip was blocked with 1% BSA in PBS containing 0.1% Triton X-100 for 60 min at room temperature, followed by overnight incubation at 4° C. with biotinylated anti-phosphotyrosine antibody at a 1:2000 dilution in PBST containing 1% BSA. After a 2 times 10 mins wash at room temperature with PBST, the slide was incubated with Cy3-labeled streptavidin at a 1:2000 dilution in PBST containing 1% BSA. Thereafter, the slide was washed 3 times 15 minutes at room temperature in PBST. After a short rinse with distilled water, the slide was air dried and scanned using a GSI Lumonics scanner. The results showed the presence of fluorescent signal at those locations containing phosphotyrosine and not at other locations, including those containing phosphoserine, and indicate that the phosphopeptide, despite isocyanate binding to the hydrogel, retained its appropriate native conformation to allow recognition by the antibody.

EXAMPLE 11

Dephosphorylation of Tyrosine Phosphorylated Peptides on a Biochip with Tyrosine Phosphatases The previous examples demonstrated the use of the hydrogel matrix to support binding interactions of extended natures (for minutes or hours). The following experiment shows that the matrix also supports transient binding interactions, such as those involving enzymatic activity, as well. In this example, a phosphopeptide substrate is anchored within the hydrogel matrix, which then serves as a substrate for an enzyme that removes the phosphate group. Residual phosphates are then detected using the methodology of Example 10.

Using the same experimental procedure as described in Example 10, printed slides were incubated with either 6 units Leucocyte Antigene Related (LAR) protein tyrosin phosphatase or 6 units *Yersinia enterocolitica* (YOP) protein tyrosine phosphatase in supplied reaction buffer (1×LAR-buffer:25 mM Tris-HCl, 50 mM NaCl, 2 mM Na$_2$EDTA, 5 mM dithiothreitol, 0.01% Brij-35, pH 7.0 at 25° C.; 1×YOB-buffer: 50 mM Tris-HCl, 100 mM NaCl, 2 mM Na$_2$EDTA, 5 mM dithiothreitol, 0.01% Brij-35, pH 7.0 at 25° C.) in a 430 µL chamber for 10 minutes at room temperature. Thereafter, the chamber was removed, and the glass slides were moved to a glass slide-staining dish. The reaction was stopped by washing the slides 2×10 min at room temperature with 1 mM sodium pervanadate (universal tyrosine phosphatase inhibitor) in PBST. Thereafter, the slides were blocked with 1% BSA, incubated with biotinylated anti-phosphotyrosine antibody followed by Cy3-streptavidin binding as described in Example 10. Loss of fluorescent signal earlier observed in Example 10 indicated the ability of the phosphorylase enzyme to enter the hydrogel, maintain its biological activity and transiently interact with one or more substrates, i.e. the anchored phosphopeptides. More specifically, the results show that the LAR-PTPase selectively removes the phosphate group substantially completely from Peptide No. 1 and to a lesser degree on the remaining peptides that contain a pTyr residue. The YOB-PTPase enzyme substantially completely removes the phosphate group from Peptides Nos. 1, 3, 6, 8 and 13; it removes the phosphate group significantly from Peptides Nos. 2, 7, 10, 14 and 15, i.e. to a greater degree than does the LAR-PTPase for those peptides. Thus, the fluorescence results with the various phosphopeptides indicated a preferential specificity on the part of the two phosphorylase enzymes towards certain of the phosphopeptide sequences.

EXAMPLE 12

Metal Chelator

Binding entities need not be biological in origin, but a variety of synthetic molecules can be employed as well. In this example, a metal chelator is used to anchor a metal ion within the hydrogel matrix where it serves to bind multiple histidine moieties present within a protein molecule.

$Ni^{++}$ or $Cu^{++}$NTA hydrogel is generated by mixing various amount of nitrilotriacetic acid with HYPOL™ solution and spotted on a glass slide. The polymerized gel spots are washed with 50 mM acetic acid in dH$_2$O, charged with 50 mM Cu(NO$_3$)$_2$ or Ni(NO$_3$)$_2$; they are then washed with 50 mM acetic acid in dH$_2$O containing 0.1M KNO3 (pH4.0) and finally rinsed with dH$_2$O 6×His tagged green fluorescent protein at 10 µg/ml in PBST containing 1% BSA was added to the slide, which was imaged in PBS by a home-built CCD camera under proper excitation and emission filter, after the removal of free unbound 6×His-GFP. An increased fluorescent signal is observed that corresponds with increased chelator and indicates that the hydrogel matrix supports the use of small molecules as intermediate binding agents.

EXAMPLE 13

Alpha-2-macroglobulin-trypsin Interaction on a Biochip (Electric Field Based Loading)

Alpha-2-macroglobulin is a large plasma protein (mw 800,000) that circulates in the blood specifically to bind to and neutralize proteases, a mechanism which protects the body from excessive protease activity, essentially preventing the body from "digesting" itself. The association between alpha-2-macroglobulin and proteases like trypsin is very strong, and alpha-2-macroglobulin immobilized to agarose beads has been used to affinity-purify trypsin and other proteases.

Three sets of hydrogel microdroplets were spotted onto amine-derivatized glass. The glass slide was first treated with 1% BSA solution in 10 mM sodium phosphate buffer and 150 mM NaCl (PBS), pH 7.4, for 2 hours at room temperature to block nonspecific binding sides. Failure to do so would result in some fluorescein-labeled protein binding nonspecifically, thus raising the signal-to-noise ratio. The hydrogel consisted of a prepolymer comprising isocyanate-functional HYPOL™. Polymerization was initiated with an aqueous solution, and the polymerization kinetics were controlled by pH and temperature. Each hydrogel microdroplet was caused to polymerize at a controlled rate to prevent opacity due to $CO_2$ gas evolution, forming one cell of the microarray. A first set such of hydrogel cells is loaded with α-2-macroglobulin using a solution of 50 μL at a concentration of 5 mg/mL PBS. The high molecular weight of α-2-macroglobulin limits rapid diffusion into the hydrogel droplet, and the diffusion rate is increased by using a mild electrical current (2.5-5 mV) delivered by a small electrode system. Once α-2-macroglobulin has diffused inside the hydrogel droplet, its large molecular weight prevents significant subsequent diffusion from the droplet. Ferritin is used to provide a negative control protein as it is known not to bind to trypsin. Ferritin is similarly diffused into a second set of hydrogel droplets using the same electrode system and mild electrical current under the same conditions. A third set of droplets is not treated with any protein and serves as an additional negative control. All three sets of droplets are then exposed to FITC-labeled trypsin for about 15 minutes and washed with 1% BSA-PBS, pH 7.4 for about 5 to 20 minutes. Fluorescence intensities are measured with a CCD camera, and results are shown in Table C.

TABLE C

Specific binding of FITC-trypsin to α-2-macroglobulin

| Immobilized Protein | Flourescence Intensity (au) |
|---|---|
| α-2-macroglobulin | 800 |
| Ferritin | 20 |
| No protein | 10 |

The results indicate that FITC-labeled trypsin specifically binds to α-2-macroglobulin, its natural ligand, within the hydrogel droplets, and that there is little detectable binding activity to either the negative control protein ferritin or to the hydrogel itself.

Although the invention has been described with respect to a number of different embodiments which include the best modes presently contemplated by the inventors, it should be understood that changes and modifications as would be obvious to one skilled in this art may be made without departing from the scope of the invention which is set forth in the claims appended hereto. For example, although particular fluorophores, such as FITC and Cy3, were used, other fluorophores or other reporters can alternatively be used. Although there are advantages in the use of biochips having a plurality of cells carrying different nonhybridization binding entities, in certain situations single-cell biochips may be suitable.

Particular features of the invention are emphasized in the claims which follow.

The invention claimed is:

1. A biochip comprising:
   a) a solid substrate having a flat top surface;
   b) a plurality of optically clear, individual, three-dimensional hydrogel cells at least 20 μm thick attached to the flat surface of the substrate at discrete locations to form an array of discrete individual three-dimensional cells protruding from said otherwise flat top surface, which hydrogel cells are formed from an isocyanate-functional prepolymer with urethane linkages; and
   c) a different binding entity immobilized within or upon various of said hydrogel cells by covalent linkage of said binding entity or an intermediate agent with reactive isocyanate groups of said hydrogel, which entity is effective to selectively hybridize to or sequester a target molecule.

2. The biochip of claim 1 wherein the hydrogel comprises polyethylene glycol, polypropylene glycol, or copolymers thereof having a molecular weight of about 5000.

3. The biochip according to claim 2, wherein the three-dimensional individual hydrogel cells are between about 30 μm and about 100 μm thick.

4. The biochip according to claim 1, wherein said binding entity is directly covalently bound to and within the hydrogel cell through reaction with the isocyanate groups.

5. The biochip of claim 1 wherein about 15% to about 5% of the reactive isocyanates in said prepolymer that forms said cell have reacted to immobilize said binding entities or said intermediate agents.

6. The biochip of claim 1 wherein each said binding entity comprises DNA, RNA or PNA.

7. The biochip of claim 1 wherein each said binding entity comprises an immunoglobin, an enzyme, a receptor, an enzyme inhibitor, an enzyme substrate, or a peptide.

8. The biochip of claim 7 wherein each said binding entity is immobilized within the hydrogel through an interaction with an intermediate agent.

9. The biochip of claim 1 wherein the substrate is optically transparent and has reactive molecules on its top surface to which the hydrogel is covalently bound through some of said isocyanate groups of the polymer.

10. A hydrogel biochip comprising:
    a) a solid substrate having a flat top surface;
    b) a plurality of optically clear, individual, three-dimensional hydrogel cells of an isocyanate-functional hydrogel at least about 20 μm thick, comprising polyethylene glycol, polypropylene glycol, or copolymers thereof having urethane linkages, bound to the top surface of said substrate at discrete locations to form an array of discrete individual three-dimensional cells protruding from said otherwise flat top surface;
    c) intermediate agents immobilized within or upon said hydrogel cells by covalent binding to reactive isocyanate groups of said hydrogel; and
    d) different protein binding entities bound to said intermediate agents respectively within at least several of said hydrogel cells by interaction therewith in a manner so that said protein binding entities assume their native conformations.

11. A biochip comprising:
    a) a solid substrate having a flat top surface;
    b) a plurality of optically clear, individual, three-dimensional hydrogel cells at least about 20 μm thick attached to the surface of the substrate at discrete locations to form an array of discrete individual three-dimensional cells protruding from said otherwise flat top surface, each hydrogel cell being a polymer formed from an isocyanate-functional urethane prepolymer; and
    c) different protein binding entities immobilized via linkage to isocyanate groups of said hydrogel within or upon different said hydrogel cells, each protein binding entity being effective to selectively hybridize to or sequester a target molecule.

12. The biochip of claim 11 wherein the hydrogel comprises polyethylene glycol, polypropylene glycol, or copolymers thereof having a molecular weight of at least about 5000 with urethane linkages to polyisocyanates.

13. The biochip of claim 12 wherein each hydrogel cell is between about 20 μm and about 100 μm thick.

14. The biochip of claim 11 wherein each said protein binding entity is directly covalently bound to and within the hydrogel cells through reaction with isocyanate groups of said prepolymer that forms said hydrogel.

15. The biochip of claim 11 wherein with said protein binding entities comprise immunoglobins or aptamers.

16. A biochip comprising:
    a) a solid substrate having a flat top surface;
    b) a plurality of optically clear, individual, three-dimensional hydrogel cells at least 20 μm thick comprising urethane polymers of (i) polyethylene glycol, polypropylene glycol, or copolymers thereof and (ii) polyisocyanates, which polymers are isocyanate-functional, and which cells are bound to the flat top surface of said substrate at discrete locations to form an array of discrete individual three-dimensional cells protruding from said otherwise flat top surface;
    c) intermediate agents immobilized within or upon said hydrogel cells by covalent linkage to reactive isocyanate groups of said hydrogel; and
    d) different protein binding entities bound to said intermediate agents within at least several of said hydrogel cells by interaction therewith in a manner so that said protein binding entities can assume their native conformations.

17. The biochip of claim 16 wherein said hydrogel is a urethane-based polymer formed from a prepolymer with excess isocyanate groups in an amount of about 0.2 meq/g to about 0.8 meq/g, and wherein said protein binding entities are bound through pairs of intermediate coupling agents.

18. The biochip of claim 16 wherein said intermediate agent is nitrilotriacetic acid.

19. A biochip comprising:
    a) a solid substrate having a flat top surface that is derivatized with groups reactive with isocyanate;

b) a plurality of optically clear, individual, three-dimensional hydrogel cells at least 20 μm thick bound to the flat surface of the substrate at discrete locations which form an array of discrete individual three-dimensional cells protruding from said otherwise flat top surface, said hydrogel cells being formed from an isocyanate-functional urethane prepolymer wherein up to about 5% of its isocyanate groups are covalently bound to said derivatized groups of said substrate; and c) a different binding entity immobilized within or upon various of said hydrogel cells by covalent linkage of said binding entity or an intermediate agent with reactive isocyanate groups of said prepolymer that forms said hydrogel, said entity being effective to selectively hybridize to or sequester a target molecule.

* * * * *

UNITED STATES PATENT AND TRADEMARK OFFICE
CERTIFICATE OF CORRECTION

PATENT NO. : 7,638,464 B2
APPLICATION NO. : 10/054728
DATED : December 29, 2009
INVENTOR(S) : Fagnani et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1033 days.

Signed and Sealed this

Ninth Day of November, 2010

David J. Kappos
*Director of the United States Patent and Trademark Office*

SEQUENCE LISTING

<160> NUMBER OF SEQ ID NOS: 45

<210> SEQ ID NO 1
<211> LENGTH: 12
<212> TYPE: DNA
<213> ORGANISM: Homo Sapiens

<400> SEQUENCE: 1
cattgctcaa ac                                          12

<210> SEQ ID NO 2
<211> LENGTH: 16
<212> TYPE: DNA
<213> ORGANISM: Homo Sapiens

<400> SEQUENCE: 2
ccgtttgagc aatgat                                      16

<210> SEQ ID NO 3
<211> LENGTH: 12
<212> TYPE: DNA
<213> ORGANISM: Homo Sapiens

<400> SEQUENCE: 3
cctaagttca tc                                          12

<210> SEQ ID NO 4
<211> LENGTH: 12

```
<212> TYPE: DNA
<213> ORGANISM: Homo Sapiens

<400> SEQUENCE: 4
tatctcttat ag                                                         12

<210> SEQ ID NO 5
<211> LENGTH: 12
<212> TYPE: DNA
<213> ORGANISM: Homo Sapiens

<400> SEQUENCE: 5
ctatcgtact ga                                                         12

<210> SEQ ID NO 6
<211> LENGTH: 12
<212> TYPE: DNA
<213> ORGANISM: Homo Sapiens

<400> SEQUENCE: 6
ttccttcacg ag                                                         12

<210> SEQ ID NO 7
<211> LENGTH: 12
<212> TYPE: DNA
<213> ORGANISM: Homo Sapiens

<400> SEQUENCE: 7
attattccac gg                                                         12

<210> SEQ ID NO 8
<211> LENGTH: 12
<212> TYPE: DNA
<213> ORGANISM: Homo Sapiens

<400> SEQUENCE: 8
atctccgaac ta                                                         12

<210> SEQ ID NO 9
<211> LENGTH: 12
<212> TYPE: DNA
<213> ORGANISM: Homo Sapiens

<400> SEQUENCE: 9
ccttattatg ca                                                         12

<210> SEQ ID NO 10
<211> LENGTH: 12
<212> TYPE: DNA
<213> ORGANISM: Homo Sapiens

<400> SEQUENCE: 10
acgcttcctc ag                                                         12

<210> SEQ ID NO 11
<211> LENGTH: 12
<212> TYPE: DNA
<213> ORGANISM: Homo Sapiens

<400> SEQUENCE: 11
gacttccatc gg                                                         12

<210> SEQ ID NO 12
```

-continued

```
<211> LENGTH: 12
<212> TYPE: DNA
<213> ORGANISM: Homo Sapiens

<400> SEQUENCE: 12
cgtaccttgt aa                                                           12

<210> SEQ ID NO 13
<211> LENGTH: 12
<212> TYPE: DNA
<213> ORGANISM: Homo Sapiens

<400> SEQUENCE: 13
ctaaacctcc aa                                                           12

<210> SEQ ID NO 14
<211> LENGTH: 12
<212> TYPE: DNA
<213> ORGANISM: Homo Sapiens

<400> SEQUENCE: 14
ctagctatct gg                                                           12

<210> SEQ ID NO 15
<211> LENGTH: 12
<212> TYPE: DNA
<213> ORGANISM: Homo Sapiens

<400> SEQUENCE: 15
taattccatt gc                                                           12

<210> SEQ ID NO 16
<211> LENGTH: 12
<212> TYPE: DNA
<213> ORGANISM: Homo Sapiens

<400> SEQUENCE: 16
attccgatcc ag                                                           12

<210> SEQ ID NO 17
<211> LENGTH: 12
<212> TYPE: DNA
<213> ORGANISM: Homo Sapiens

<400> SEQUENCE: 17
ttagttattc ga                                                           12

<210> SEQ ID NO 18
<211> LENGTH: 12
<212> TYPE: DNA
<213> ORGANISM: Homo Sapiens

<400> SEQUENCE: 18
aagttcatct cc                                                           12

<210> SEQ ID NO 19
<211> LENGTH: 12
<212> TYPE: DNA
<213> ORGANISM: Homo Sapiens

<400> SEQUENCE: 19
ttcatctccg aa                                                           12
```

<210> SEQ ID NO 20
<211> LENGTH: 12
<212> TYPE: DNA
<213> ORGANISM: Homo Sapiens

<400> SEQUENCE: 20
ccgaactaaa cc                                                              12

<210> SEQ ID NO 21
<211> LENGTH: 12
<212> TYPE: DNA
<213> ORGANISM: Homo Sapiens

<400> SEQUENCE: 21
aactaaacct cc                                                              12

<210> SEQ ID NO 22
<211> LENGTH: 12
<212> TYPE: DNA
<213> ORGANISM: Homo Sapiens

<400> SEQUENCE: 22
ctaaacgtcc aa                                                              12

<210> SEQ ID NO 23
<211> LENGTH: 30
<212> TYPE: DNA
<213> ORGANISM: Homo Sapiens

<400> SEQUENCE: 23
ttggaggttt agttcggaga tgaacttagg                                           30

<210> SEQ ID NO 24
<211> LENGTH: 32
<212> TYPE: DNA
<213> ORGANISM: Homo Sapiens

<400> SEQUENCE: 24
tttacggtag aggtcactgt gacctctacc cg                                        32

<210> SEQ ID NO 25
<211> LENGTH: 32
<212> TYPE: DNA
<213> ORGANISM: Homo Sapiens

<400> SEQUENCE: 25
tttacggtag aggtcactgt atggtctacc cg                                        32

<210> SEQ ID NO 26
<211> LENGTH: 12
<212> TYPE: PRT
<213> ORGANISM: Homo Sapiens
<220> FEATURE:
<221> NAME/KEY: misc_feature
<222> LOCATION: (5)..(5)
<223> OTHER INFORMATION: Xaa is pTyr

<400> SEQUENCE: 26

Thr Arg Asn Ile Xaa Gln Thr Asn Tyr Tyr Arg Lys
1               5                   10

<210> SEQ ID NO 27
<211> LENGTH: 11
<212> TYPE: PRT
<213> ORGANISM: Homo Sapiens -continued

```
<220> FEATURE:
<221> NAME/KEY: misc_feature
<222> LOCATION: (5)..(5)
<223> OTHER INFORMATION: Xaa is pTyr

<400> SEQUENCE: 27

Asp Ala Asp Glu Xaa Leu Ile Pro Gln Gln Gly
1               5                   10

<210> SEQ ID NO 28
<211> LENGTH: 10
<212> TYPE: PRT
<213> ORGANISM: Homo Sapiens
<220> FEATURE:
<221> NAME/KEY: misc_feature
<222> LOCATION: (4)..(4)
<223> OTHER INFORMATION: Xaa is pTyr

<400> SEQUENCE: 28

Glu Asn Asp Xaa Leu Ile Asn Ala Ser Leu
1               5                   10

<210> SEQ ID NO 29
<211> LENGTH: 12
<212> TYPE: PRT
<213> ORGANISM: Homo Sapiens

<400> SEQUENCE: 29

Thr Arg Asn Ile Tyr Gln Thr Asn Tyr Tyr Arg Lys
1               5                   10

<210> SEQ ID NO 30
<211> LENGTH: 13
<212> TYPE: PRT
<213> ORGANISM: Homo Sapiens

<400> SEQUENCE: 30

Thr Ser Thr Gly Pro Gln Tyr Gln Pro Gly Glu Asn Leu
1               5                   10

<210> SEQ ID NO 31
<211> LENGTH: 13
<212> TYPE: PRT
<213> ORGANISM: Homo Sapiens
<220> FEATURE:
<221> NAME/KEY: misc_feature
<222> LOCATION: (7)..(7)
<223> OTHER INFORMATION: Xaa is pTyr

<400> SEQUENCE: 31

Thr Ser Thr Glu Pro Gln Xaa Gln Pro Gly Gly Asn Leu
1               5                   10

<210> SEQ ID NO 32
<211> LENGTH: 11
<212> TYPE: PRT
<213> ORGANISM: Homo Sapiens
<220> FEATURE:
<221> NAME/KEY: misc_feature
<222> LOCATION: (4)..(4)
<223> OTHER INFORMATION: Xaa is pTyr

<400> SEQUENCE: 32

Ser Val Leu Xaa Thr Ala Val Gln Pro Asn Glu
1               5                   10

<210> SEQ ID NO 33
```

```
<211> LENGTH: 13
<212> TYPE: PRT
<213> ORGANISM: Homo Sapiens
<220> FEATURE:
<221> NAME/KEY: misc_feature
<222> LOCATION: (9)..(9)
<223> OTHER INFORMATION: Xaa is pTyr

<400> SEQUENCE: 33

Arg Arg Leu Ile Glu Asp Asn Glu Xaa Thr Ala Arg Gly
1               5                   10

<210> SEQ ID NO 34
<211> LENGTH: 12
<212> TYPE: PRT
<213> ORGANISM: Homo Sapiens
<220> FEATURE:
<221> NAME/KEY: misc_feature
<222> LOCATION: (7)..(7)
<223> OTHER INFORMATION: Xaa is pSer

<400> SEQUENCE: 34

Arg Arg Arg Glu Glu Glu Xaa Glu Glu Glu Ala Ala
1               5                   10

<210> SEQ ID NO 35
<211> LENGTH: 8
<212> TYPE: PRT
<213> ORGANISM: Homo Sapiens
<220> FEATURE:
<221> NAME/KEY: misc_feature
<222> LOCATION: (4)..(4)
<223> OTHER INFORMATION: Xaa is pTyr

<400> SEQUENCE: 35

Asp Arg Val Xaa Ile His Pro Phe
1               5

<210> SEQ ID NO 36
<211> LENGTH: 13
<212> TYPE: PRT
<213> ORGANISM: Homo Sapiens

<400> SEQUENCE: 36

Thr Ser Thr Glu Pro Gln Tyr Gln Pro Gly Glu Asn Leu
1               5                   10

<210> SEQ ID NO 37
<211> LENGTH: 13
<212> TYPE: PRT
<213> ORGANISM: Homo Sapiens

<400> SEQUENCE: 37

Arg Arg Leu Ile Glu Asp Ala Glu Tyr Ala Ala Arg Gly
1               5                   10

<210> SEQ ID NO 38
<211> LENGTH: 13
<212> TYPE: PRT
<213> ORGANISM: Homo Sapiens
<220> FEATURE:
<221> NAME/KEY: misc_feature
<222> LOCATION: (9)..(9)
<223> OTHER INFORMATION: Xaa is pTyr

<400> SEQUENCE: 38

Arg Arg Leu Ile Glu Asp Ala Glu Xaa Ala Ala Arg Gly
1               5                   10
```

<210> SEQ ID NO 39
<211> LENGTH: 10
<212> TYPE: PRT
<213> ORGANISM: Homo Sapiens
<220> FEATURE:
<221> NAME/KEY: misc_feature
<222> LOCATION: (2)..(2)
<223> OTHER INFORMATION: Xaa is pTyr

<400> SEQUENCE: 39

Asn Xaa Ile Ser Lys Gly Ser Thr Phe Leu
1               5                   10

<210> SEQ ID NO 40
<211> LENGTH: 12
<212> TYPE: PRT
<213> ORGANISM: Homo Sapiens
<220> FEATURE:
<221> NAME/KEY: misc_feature
<222> LOCATION: (7)..(7)
<223> OTHER INFORMATION: Xaa is pTyr

<400> SEQUENCE: 40

Cys Asn Val Val Pro Leu Xaa Asp Leu Leu Glu
1               5                   10

<210> SEQ ID NO 41
<211> LENGTH: 13
<212> TYPE: PRT
<213> ORGANISM: Homo Sapiens

<400> SEQUENCE: 41

Arg Arg Leu Ile Glu Asp Asn Glu Thr Thr Ala Arg Gly
1               5                   10

<210> SEQ ID NO 42
<211> LENGTH: 13
<212> TYPE: PRT
<213> ORGANISM: Homo Sapiens

<400> SEQUENCE: 42

Arg Arg Leu Ile Glu Asp Ala Glu Thr Ala Ala Arg Gly
1               5                   10

<210> SEQ ID NO 43
<211> LENGTH: 10
<212> TYPE: PRT
<213> ORGANISM: Homo Sapiens

<400> SEQUENCE: 43

Thr Phe Gln Ala Tyr Pro Leu Arg Glu Ala
1               5                   10

<210> SEQ ID NO 44
<211> LENGTH: 8
<212> TYPE: PRT
<213> ORGANISM: Homo Sapiens

<400> SEQUENCE: 44

Gly Gly Val Tyr Val His Pro Val
1               5

<210> SEQ ID NO 45
<211> LENGTH: 10
<212> TYPE: PRT

```
-continued

<213> ORGANISM: Homo Sapiens

<400> SEQUENCE: 45

Asp Arg Val Tyr Ile His Pro Phe His Leu
1               5                   10
```